US012564594B2

(12) United States Patent
Kitayama et al.

(10) Patent No.: US 12,564,594 B2
(45) Date of Patent: Mar. 3, 2026

(54) PHARMACEUTICAL COMPOSITION CONTAINING 9-ETHYL-6, 6-DIMETHYL-8-(4-MORPHOLIN-4-YL-PIPERIDIN-1-YL)-11-OXO-6, 11-DIHYDRO-5H-BENZO[B]CARBAZOLE-3-CARBONITRILE

(71) Applicant: Chugai Seiyaku Kabushiki Kaisha, Tokyo (JP)

(72) Inventors: Akira Kitayama, Tokyo (JP); Takeshi Sasoh, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 1289 days.

(21) Appl. No.: 17/255,707

(22) PCT Filed: Jun. 28, 2019

(86) PCT No.: PCT/JP2019/025856
§ 371 (c)(1),
(2) Date: Jun. 8, 2021

(87) PCT Pub. No.: WO2020/004630
PCT Pub. Date: Jan. 2, 2020

(65) Prior Publication Data

US 2021/0290630 A1 Sep. 23, 2021

(30) Foreign Application Priority Data

Jun. 29, 2018 (JP) ................................ 2018-124830

(51) Int. Cl.
*A61K 31/5377* (2006.01)
*A61K 9/20* (2006.01)

(52) U.S. Cl.
CPC ........ *A61K 31/5377* (2013.01); *A61K 9/2009* (2013.01); *A61K 9/2013* (2013.01);
(Continued)

(58) Field of Classification Search
CPC .............. A61K 31/5377; A61K 9/2009; A61K 9/2013; A61K 9/2018; A61K 9/2027; A61K 9/2054
See application file for complete search history.

(56) References Cited

U.S. PATENT DOCUMENTS 5,182,289 A 1/1993 Ting et al.
5,296,454 A 3/1994 Goto et al.
(Continued)

FOREIGN PATENT DOCUMENTS

CN 1902200 A 1/2007
EA 001450 B1 4/2001
(Continued)

OTHER PUBLICATIONS

Bilsland et al., "Behavioral and Neurochemical Alterations in Mice Deficient in Anaplastic Lymphoma Kinase Suggest Therapeutic Potential for Psychiatric Indications," Neuropsychopharmacology, 2008, 33:685-700.

(Continued)

*Primary Examiner* — Clinton A Brooks
*Assistant Examiner* — Kyle Nottingham
(74) *Attorney, Agent, or Firm* — Foley & Lardner LLP

(57) ABSTRACT

The present invention aims to provide a high-dose formulation with improved properties of a pharmaceutical composition comprising a poorly soluble basic agent, particularly a compound represented by formula (I) or a salt thereof. The problem described above can be solved by providing a pharmaceutical composition comprising the compound represented by formula (I) or a salt thereof, a surfactant, and a basic substance.

16 Claims, 3 Drawing Sheets

(52) U.S. Cl.
CPC .......... *A61K 9/2018* (2013.01); *A61K 9/2027* (2013.01); *A61K 9/2054* (2013.01)

(56) References Cited

U.S. PATENT DOCUMENTS

| | | | | |
|---|---|---|---|---|
| 5,721,267 | A | 2/1998 | Broka | |
| 5,936,084 | A | 8/1999 | Jirousek et al. | |
| 9,126,931 | B2 | 9/2015 | Kinoshita et al. | |
| 9,365,514 | B2 | 6/2016 | Furumoto et al. | |
| 9,440,922 | B2 | 9/2016 | Kinoshita et al. | |
| 9,714,229 | B2 | 7/2017 | Tanaka et al. | |
| 10,344,014 | B2 | 7/2019 | Shiraki et al. | |
| 10,350,214 | B2 * | 7/2019 | Tomimatsu ............ | A61K 47/20 |
| 11,433,076 | B2 * | 9/2022 | Tomimatsu ............. | A61P 25/00 |
| 2004/0072890 | A1 | 4/2004 | Munro et al. | |
| 2005/0107364 | A1 | 5/2005 | Hutchinson et al. | |
| 2006/0063790 | A1 | 3/2006 | Gillman et al. | |
| 2007/0031907 | A1 | 2/2007 | Pinna et al. | |
| 2007/0099893 | A1 | 5/2007 | Boyd et al. | |
| 2007/0249653 | A1 | 10/2007 | Jagtap et al. | |
| 2008/0058320 | A1 | 3/2008 | Herold et al. | |
| 2008/0090776 | A1 | 4/2008 | Mano et al. | |
| 2008/0095838 | A1 | 4/2008 | Abou Chacra-Vernet | |
| 2008/0262021 | A1 | 10/2008 | Capraro et al. | |
| 2008/0287456 | A1 | 11/2008 | Roberts et al. | |
| 2009/0099193 | A1 | 4/2009 | Mano et al. | |
| 2009/0221555 | A1 | 9/2009 | Ahmed et al. | |
| 2010/0099658 | A1 | 4/2010 | Kondoh et al. | |
| 2010/0240673 | A1 | 9/2010 | Mano et al. | |
| 2011/0230545 | A1 | 9/2011 | Mano et al. | |
| 2012/0083488 | A1 | 4/2012 | Kinoshita et al. | |
| 2013/0065885 | A1 | 3/2013 | Roberts et al. | |
| 2013/0143877 | A1 | 6/2013 | Furumoto et al. | |
| 2013/0158095 | A1 | 6/2013 | Mano et al. | |
| 2015/0150845 | A1 | 6/2015 | Kinoshita et al. | |
| 2015/0184161 | A1 | 7/2015 | Mano et al. | |
| 2015/0272958 | A1 | 10/2015 | Kodama et al. | |
| 2016/0317494 | A1 | 11/2016 | Furumoto et al. | |
| 2016/0340308 | A1 | 11/2016 | Kinoshita et al. | |
| 2017/0035773 | A1 | 2/2017 | Tomimatsu et al. | |
| 2017/0081306 | A1 | 3/2017 | Tanaka et al. | |
| 2017/0119781 | A1 | 5/2017 | Meier et al. | |
| 2017/0217927 | A1 | 8/2017 | Shiraki et al. | |
| 2018/0066266 | A1 | 3/2018 | Mano et al. | |
| 2019/0284163 | A1 | 9/2019 | Shiraki et al. | |
| 2020/0000707 | A1 | 1/2020 | Roberts et al. | |
| 2020/0017442 | A1 | 1/2020 | Kinoshita et al. | |
| 2020/0038407 | A1 | 2/2020 | Tomimatsu et al. | |
| 2020/0246349 | A1 | 8/2020 | Kodama et al. | |
| 2021/0052550 | A1 | 2/2021 | Furumoto et al. | |
| 2023/0105990 | A1 * | 4/2023 | Tomimatsu ............ | A61K 47/38 424/489 |
| 2023/0398096 | A1 | 12/2023 | Furumoto et al. | |

FOREIGN PATENT DOCUMENTS

| | | | |
|---|---|---|---|
| EP | 2 253 318 | | 11/2010 |
| EP | 2 606 886 | A1 | 6/2013 |
| EP | 3 135 287 | A1 | 3/2017 |
| JP | 08-092090 | A | 4/1996 |
| JP | 2007-504270 | A | 3/2007 |
| JP | 2008-500288 | A | 1/2008 |
| JP | 2009-100783 | A | 5/2009 |
| JP | 4588121 | B1 | 11/2010 |
| JP | 4918630 | B1 | 4/2012 |
| JP | 5006987 | B2 | 7/2012 |
| JP | 5859712 | B1 | 2/2016 |
| RU | 2162089 | C2 | 1/2001 |
| WO | WO-00/69856 | A1 | 11/2000 |
| WO | WO-2004/080980 | A1 | 9/2004 |
| WO | WO-2005/009389 | A2 | 2/2005 |
| WO | WO-2005/023228 | A1 | 3/2005 |
| WO | WO-2005/097765 | A1 | 10/2005 |
| WO | WO-2006/021884 | A2 | 3/2006 |
| WO | WO-2007/023310 | A2 | 3/2007 |
| WO | WO-2007/056497 | A1 | 5/2007 |
| WO | WO-2007/130468 | A2 | 11/2007 |
| WO | WO-2008/021369 | A2 | 2/2008 |
| WO | WO-2008/051547 | A1 | 5/2008 |
| WO | WO-2008/130951 | A1 | 10/2008 |
| WO | WO-2009/008371 | A1 | 1/2009 |
| WO | WO-2009/013126 | A1 | 1/2009 |
| WO | WO-2009/073620 | A2 | 6/2009 |
| WO | WO-2010/128324 | A1 | 11/2010 |
| WO | WO-2010/142423 | A2 | 12/2010 |
| WO | WO-2010/142685 | A1 | 12/2010 |
| WO | WO-2012/023597 | A1 | 2/2012 |
| WO | WO-2012/042421 | A1 | 4/2012 |
| WO | WO-2015/016256 | A1 | 2/2015 |
| WO | WO-2015/163448 | A1 | 10/2015 |
| WO | WO-2016/021707 | A1 | 2/2016 |

OTHER PUBLICATIONS

Soda et al., "Identification of the transforming EML4-ALK fusion gene in non-small-cell lung cancer," Nature, Aug. 2, 2007, 448:561-567.

Yamamura, Tadahiro, "Study on stability of main drug by external lubricant method and evaluation for distribution of lubricant," Thesis, Major in Drug Discovery of Biopharmaceutical Sciences, Graduate School and Faculty of Pharmaceutical Sciences, Chiba University, 2009, pp. 1-72, with partial English translation.

U.S. Appl. No. 16/862,125, filed Apr. 29, 2020, Kinoshita et al.

U.S. Appl. No. 17/019,896, filed Sep. 14, 2020, Shiraki et al.

U.S. Appl. No. 17/271,437, filed Sep. 3, 2019, Serizawa et al.

Asche et al., "Synthesis, antitumour activity and structure-activity relationships of 5H-benzo[b]carbazoles," Bioorganic & Medicinal Chemistry, 2005, 13:819-837.

Bernardo et al., "Synthesis, Electrochemistry, and Bioactivity of the Cyanobacterial Calothrixins and Related Quinones," J. Med. Chem., 2004, 47:4958-4963.

Boogaard et al., "Ring D Modifications of Ellipticine. Part 2. Chlorination of Ellipticine via its N-oxide and Synthesis and Selective Oxidation of 5,6, 11-Trimethyl-5H-Benzo[b]Carbazole," Tetrahedron, 1994, 50(16):4811-4828.

Bunz, F., "Chapter 1, The Genetic Basis of Cancer," Principles of Cancer Genetics, 2008, 1-47.

CAS RN 100863-39-6, STN Entry Date Mar. 15, 1986.

CAS RN 222318-66-3, STN Entry Date May 7, 1999.

CAS RN 24716-14-1, STN Entry Date Nov. 16, 1984.

CAS RN 36263-63-5, STN Entry Date Nov. 16, 1984.

CAS RN 4355-38-8, STN Entry Date Nov. 16, 1984.

CAS RN 6008-29-3, STN Entry Date Nov. 16, 1984.

CAS RN 61492-49-7, STN Entry Date Nov. 16, 1984.

CAS RN 74205-47-3, STN Entry Date Nov. 16, 1984.

CAS RN 89579-57-7, STN Entry Date Nov. 16, 1984.

CAS RN 93257-39-7, STN Entry Date Dec. 18, 1984.

Chang et al., "Polymethacrylates," Handbook of Pharmaceutical Excipients, Rowe et al., Eds., 2009, 6th Ed., 525-533.

Chen et al., "Oncogenic mutations of ALK kinase in neuroblastoma," Nature, Oct. 16, 2008, 455:971-974, and Methods page.

Cools et al., "Identification of Novel Fusion Partners of ALK, the Anaplastic Lymphoma Kinase, in Anaplastic Large-Cell Lymphoma and Inflammatory Myofibroblastic Tumor," Genes, Chromosomes & Cancer, 2002, 34:354-362.

Database Accession No. 1:1259(XP55784247), RN 826-55-1, 1907, one page.

Database Accession No. 27:43772 (XP55784257), RN 37828-19-6 CA, 1933, one page.

Database Accession No. 28:22560 (XP55784253), RN 77-55-4, 1934, one page.

Database Accession No. 28:22560 (XP55784254), RN 1135-67-7, 1934, one page.

Database Accession No. 41:3570(XP55784249), RN 6120-95-2, 1946, one page.

Davies, Peter, "Oral Solid Dosage Forms," Drugs and the Pharmaceutical Sciences, Pharmaceutical Preformulation and Formulation, Mark Gibson, Ed., 2009, 2nd Edition, 199:367-430.

(56) References Cited

OTHER PUBLICATIONS

Defendant Fresenius Kabi USA, LLC's Initial Invalidity Contentions, filed Oct. 9, 2020 in C.A. No. 20-394 (RGA), *Hoffmann-LaRoche, Inc., Chugai Pharmaceutical Co., Ltd., and Genentech, Inc.* (*Plaintiffs and Counterclaim Defendants*) v. *Fresenius Kabi USA, LLC* (*Defendant and Counterclaim Plantiff*), 112 pages.

Druker et al., "Section 1: Chronic Myelogenous Leukemia," Cancer: Principles & Practice of Oncology, 7th Edition (DeVita et al., Eds.), 2121.

Faderl et al., "Section 3: Myelodysplastic Syndromes," Cancer: Principles & Practice of Oncology, 7th Edition (DeVita et al., Eds.), 2144.

Fine et al., "Section 2: Neoplasms of the Central Nervous System," Cancer: Principles & Practice of Oncology, 7th Edition (DeVita et al., Eds.), 1834-1887.

Fischer et al., "A Ki-1(CD30)-Positive Human Cell Line (Karpas 299) Established From a High-Grade Non-Hodgkin's Lymphoma, Showing a 2;5 Translocation and Rearrangement of the T-Cell Receptor B-Chain Gene," Blood, Jul. 1988, 72(1):234-240.

Gadgeel et al., "A Phase 1 Dose Escalation Study of a New ALK Inhibitor, CH5424802/RO5424802, in ALK Non-Small Cell Lung Cancer (NSCLC) Patients who have Failed Crizotinib (AF-002JG/NP28761, NCT01588028," Journal of Thoracic Oncology, Nov. 2013, 8(2):S199, Abstract O16.06.

Gadgeel et al., "Safety and activity of alectinib against systemic disease and brain metastases in patients with crizotinib-resistant ALK-rearranged non-small-cell lung cancer (AF-002JG): results from the dose-finding portion of a phase 1/2 study," Lancet Oncology, 2014, 15:1119-1128.

Galkin et al., "Identification of NVP-TAE684, a potent, selective and efficacious inhibitor of NPM-ALK," PNAS, Jan. 2, 2007, 104(1):270-275.

Galkin et al., "Identification of NVP-TAE684, a potent, selective and efficacious inhibitor of NPM-ALK," PNAS, Jan. 2, 2007, 104(1):270-275 (and Corrections published in PNAS, Feb. 6, 2007, 104(6):2024-2025).

Garbett et al., "Extending Nature's Leads: The Anticancer Agent Ellipticine," Curr. Med. Chem.—Anti-Cancer Agents, 2004, 4:149-172.

George et al., "Activating mutations in ALK provide a therapeutic target in neuroblastoma," Nature, 2008, 455:975-978.

Girouard et al., "Neurovascular coupling in the normal brain and in hypertension, stroke, and Alzheimer disease," Journal of Applied Physiology, 2006, 100:328-335.

Glick et al., "Treatment with atypical antipsychotics: new indications and new populations," Journal of Psychiatric Research, 2001, 35:187-191.

Goel et al., "Mice transgenic for BRAF V600E demonstrate phenotype affecting melanocyte and neural lineages," Proceedings of the American Association for Cancer Research, Apr. 2006, 47:#273.

Goodman & Gilman's, Chemotherapy of Neoplastic Diseases, The Pharmacological Basis of Therapeutics, Brunton et al., Eds., 2008, 11th Ed., 853-908.

Griffin et al., "Recurrent Involvement of 2p23 in Inflammatory Myofibroblastic Tumors," Cancer Research, Jun. 15, 1999, 59:2776-2780.

Gunby et al., "Structural Insights into the ATP Binding Pocket of the Anaplastic Lymphoma Kinase by Site-Directed Mutagenesis, Inhibitor Binding Analysis, and Homology Modeling," J. Med. Chem., 2006, 49:5759-5768.

Herbst et al., "ALK Gene Products in Anaplastic Large Cell Lymphomas and Hodgkin's Disease," Blood, Sep. 1, 1995, 86(5):1694-1700.

Hida et al., "Pharmacologic study (JP28927) of alectinib in Japanese patients with ALK non-small-cell lung cancer with or without prior crizotinib therapy," Cancer Science, 2016, 107:1642-1646.

Hooton, J.C., "Carboxymethylcellulose Calcium," Handbook of Pharmaceutical Excipients, Rowe et al., Eds., 6th Ed., 2009, 117-118.

Huang et al., "An in vivo model to study human GSTP1 polymorphisms in osteosarcoma," Proceedings of the American Association for Cancer Research, Apr. 2006, 47:#271.

Hübinger et al., "CD30-mediated cell cycle arrest associated with induced expression of p21CIP1/WAF1 in the anaplastic large cell lymphoma cell line Karpas 299," Oncogene, 2001, 20:590-598.

Inoue et al., "One-year Follow-up of a Phase I/II Study of a Highly Selective ALK Inhibitor CH5424802/RO5424802 in ALK-Rearranged Advanced Non-Small Cell Lung Cancer (NSCLC)," Journal of Thoracic Oncology, Nov. 2013, 8(Supp.2):S1204, Abstract P3.11-034.

Jazii et al., "Identification of squamous cell carcinoma associated proteins by proteomics and loss of beta tropomyosin expression in esophageal cancer," World J. Gastroenterol., Nov. 28, 2006, 12(44):7104-7112.

Kabir et al., "Hydroxypropyl Cellulose," Handbook of Pharmaceutical Excipients, Rowe et al., Eds., 6th Ed., 2009, 317-322.

Kashyap et al., "Fast Disintegrating Tablet: A Boon to Pediatric and Geriatric," International Journal of Pharma Professional's Research, Apr. 2011, 2(2):318-326.

Kinoshita et al., "Design and synthesis of a highly selective, orally active and potent anaplastic lymphoma kinase inhibitor (CH5424802)," Bioorganic & Medicinal Chemistry, 2012, 20:1271-1280.

Kirsch, Gilbert H., "Heterocyclic Analogues of Carbazole Alkaloids," Current Organic Chemistry, 2001, 5:507-518.

Knoelker et al., "Transition Metal Complexes in Organic Synthesis, Part 38. First Total Synthesis of Carbazomycin G and H," Tetrahedron Letters, 1997, 38(23):4051-4054.

Kuppen et al., "Tumor structure and extracellular matrix as a possible barrier for therapeutic approaches using immune cells or adenoviruses in colorectal cancer," Histochem. Cell. Biol., 2001, 115:67-72.

Kuster, Bernhard, Ed., Kinase Inhibitors, Methods and Protocols, Methods in Molecular Biology, 2012, vol. 795, Chapter 1 by Fabbro et al., "Targeting Cancer with Small-Molecular-Weight Kinase Inhibitors."

Kwak et al., "Anaplastic Lymphoma Kinase Inhibition in Non-Small-Cell Lung Cancer," The New England Journal of Medicine, Oct. 28, 2010, 363(18):1693-1703.

Lamant et al., "Establishment of a novel anaplastic large-cell lymphoma-cell line (COST) from a 'small-cell variant' of ALCL," Leukemia, 2004, 18:1693-1698.

Li et al., "Design and Synthesis of 5-Aryl-pyridone-carboxamides as Inhibitors of Anaplastic Lymphoma Kinase," J. Med. Chem., 2006, 49:1006-1015.

Li et al., "Development of Anaplastic Lymphoma Kinase (ALK) Small-Molecule Inhibitors for Cancer Therapy," Medicinal Research Reviews, 2008 (online Aug. 10, 2007), 23(3):372-412.

Liao, Jeffrey Jie-Lou, "Molecular Recognition of Protein Kinase Binding Pockets for Design of Potent and Selective Kinase Inhibitors," Journal of Medicinal Chemistry, Feb. 8, 2007, 50(3):409-424.

Lissoni et al., "Biotherapy with the pineal hormone melatonin plus aloe and myrrh tincture in untreatable metastatic cancer patients as an essence therapy of cancer," Cancer Therapy, 2009, 7:397-401.

Luo et al., "Principles of Cancer Therapy: Oncogene and Non-oncogene Addiction," Cell, Mar. 6, 2009, 136:823-837.

Mosse et al., "Identification of ALK as a major familial neuroblastoma predisposition gene," Nature, Oct. 16, 2008, 455:930-935, and Methods page.

Nakagawa et al., "A phase I/II study with a highly selective ALK inhibitor CH5424802/RO5424802 in ALK-positive non-small cell lung cancer (NSCLC) patients: Updated safety and efficacy results from AF-001JP," 49th Annual Meeting of the American Society of Clinical Oncology (ASCO), Chicago, IL, May 31, 2013-Jun. 4, 2013, poster, Abstract No. 8033.

Nakagawa et al., "Antitumor Activity of alectinib (CH5424802/RO5424802) for ALK-Rearranged NSCLC with or without Prior crizotinib Treatment in Bioequivalence Study," 49th Annual Meeting of the American Society of Clinical Oncology (ASCO), Chicago, IL, May 31, 2013-Jun. 4, 2013, poster, Abstract No. 8033.

National Cancer Institute, http://www.cancer.gov/, "A to Z List of Cancers," downloaded May 29, 2014, 22 pages.

(56) References Cited

OTHER PUBLICATIONS

O'Brien et al., "Section 2: Chronic Lymphoid Leukemias," Cancer: Principles & Practice of Oncology, 7th Edition (DeVita et al., Eds.), 2005, 2133.
O'Brien et al., "Vascular cognitive impairment," The Lancet Neurology, Feb. 2003, 2:89-98.
Ou et al., "Consistent Therapeutic Efficacy of CH5424802/RO5424802 in Brain Metastases Among Crizotinib-Refractory ALK-Positive Non-small Cell Lung Cancer (NSCLC) Patients in an Ongoing Phase I/II Study (AF-002JG/NP28761, NCT01588028)," Journal of Thoracic Oncology, Nov. 2013, 8(2):Abstract O17.07.
Pao et al., "EGF receptor gene mutations are common in lung cancers from 'never smokers' and are associated with sensitivity of tumors to gefitinib and erlotinib," PNAS, Sep. 7, 2004, 101(36):13306-13311.
Piva et al., "Ablation of oncogenic ALK is a viable therapeutic approach for anaplastic large-cell lymphomas," Blood, Jan. 2006, 107(2):689-697.
Plumb, P., "Sodium Lauryl Sulfate," Handbook of Pharmaceutical Excipients, Rowe et al., Eds., 6th Ed., 2009, 652-653.
Rosenwald et al., "t(1;2)(q21;p23) and t(2;3)(p23;q21): Two Novel Variant Translocations of the t(2;5)(p23;q35) in Anaplastic Large Cell Lymphoma," Blood, Jul. 1, 1999, 94(1):362-364.
Scheinberg et al., "Section 2: Management of Acute Leukemias," Cancer: Principles & Practice of Oncology, 7th Edition (DeVita et al., Eds.), 2005, 2088, 2092.
Seto et al., "CH5424802 (RO5424802) for patients with ALK-rearranged advanced non-small-cell lung cancer (AF-001JP study): a single-arm, open-label, phase 1-2 study," Lancet Oncology, Jun. 2013, 14:590-598.
Shah et al., "Current approaches in the treatment of Alzheimer's disease," Biomedicine & Pharmacotherapy, 2008, 62:199-207.
Shaw et al., "Targeting Anaplastic Lymphoma Kinase in Lung Cancer," Clinical Cancer Research, 2011, 17:2081-2086.
Sheridan, Robert P., "The Most Common Chemical Replacements in Drug-Like Compounds," J. Chem. Inf. Comput. Sci., 2002, 42:103-108.
Shujuan, Wang, "The new insights on the diagnosis of malignant histiocytosis," Chinese Journal of Laboratory Medicine, Jan. 30, 2005, 28(1):14-16.
Silverman, Richard B., The Organic Chemistry of Drug Design and Drug Action, Second Ed., Elsevier Academic Press, Northwestern University, Evanston, Illinois, 2004, 29-31, table 2.2.
Soda et al., "Identification of the transforming EML4-ALK fusion gene in non-small-cell lung cancer," Nature, Aug. 2, 2007, 448:561-566, and Methods page.
Soussi, Thierry, "p53 Antibodies in the Sera of Patients with Various Types of Cancer: A Review," Cancer Res., 2000, 60:1777-1788.
Stoica et al., "Identification of Anaplastic Lymphoma Kinase as a Receptor for the Growth Factor Pleiotrophin," J. Biol. Chem., May 18, 2001, 276(20:16772-16779.
Stoica et al., "Midkine Binds to Anaplastic Lymphoma Kinase (ALK) and Acts as a Growth Factor for Different Cell Types," J. Biol. Chem., Sep. 27, 2002, 277(39):35990-35998.
Vendome et al., "Molecular Modeling of Wild-Type and D816V c-Kit Inhibition Based on ATP-Competitive Binding of Ellipticine Derivatives to Tyrosine Kinases," J. Med. Chem., 2005, 48:6194-6201.
Wanner et al., "A convenient synthesis of 6-methylellipticine and 6-methylolivacine," Heterocycles, 1982, 19(12):2295-2300.
Wendling, Patrice, "Alectinib active in ALK-positive, crizotinib-refractory NSCLC," Chest Physician, Oct. 9, 2013, 4 pages.
Wood et al., "Lack of the t(2;5) or Other Mutations Resulting in Expression of Anaplastic Lymphoma Kinase Catalytic Domain in CD30+ Primary Cutaneous Lymphoproliferative Disorders and Hodgkin's Disease," Blood, Sep. 1, 1996, 88(5):1765-1770.
Zhao et al., "The progress of the research on anaplastic lymphoma kinase genetic abnormality of anaplastic large cell lymphoma," Foreign Medical Sciences (Section of Blood Transfusion and Heanatology), Oct. 15, 2004, 27(5):403-406.
Rojas et al., "Functional Assessment of Four Types of Disintegrants and their Effect on the Spironolactone Release Properties," AAPS PharmSciTech, Dec. 2012 (online Aug. 17, 2012), 13(4):1054-1062.
Aulton, M.E., Ed., Pharmaceutics The Science of Dosage Form Design, Churchill Livingstone, 2d Ed., 2002, cover and Chapter 1: "The design of dosage forms," 1-12.
Bauer et al., Pharmazeutische Technologie, 9. Auflage, Wissenschaftliche Verlagsgesellschaft, Stuttgart 2012, with partial English machine translation, 7 pages.
Bhattachar et al., "Weak bases and formation of a less soluble lauryl sulfate salt/complex in sodium lauryl sulfate (SLS) containing media," International Journal of Pharmaceutics, 2011, 412:95-98.
Desai et al., "Review of Disintegrants and the Disintegration Phenomena," Journal of Pharmaceutical Sciences, 2016, 105(9):2545-2555.
Hirano et al., "Arginine as a solubilizing agent: Application to poorly soluble drugs," Biophysics, 2014, 54(1):026-027, with English translation.
Huang et al., "Interactions between a poorly soluble cationic drug and sodium dodecyl sulfate in dissolution medium and their impact on in vitro dissolution behavior," International Journal of Pharmaceutics, 2018, 535(1-2):350-359.
Madlool et al., "Solubility, pH-Solubility Profile, pH-Rate Profile, and Kinetic Stability of the Tyrosine Kinase Inhibitor, Alectinib," Pharmaceuticals, 2024, 17(776):1-12.
Rowe, R.C. et al., Eds., Handbook of Pharmaceutical Excipients, 6th Ed., Pharmaceutical Press, London, 2009, pp. 86, 364, 393, 396 and 400, 7 pages.
Rowe, R.C. et al., Eds., Handbook of Pharmaceutical Excipients, $6^{th}$Ed., Pharmaceutical Press and American Pharmacists Association, 2009, cover pages i-iv, 393-403, 431-433 and 629-633, 24 pages.
CAS Abstract and Indexed Compound. H. Gilman et al., 68 Journal of the American Chemical Society, 1946, 522, Accession No. 1946:14703, 1 page.
Gilman et al., "Metalation of Cumene by Ethylpotassium," Journal of the American Chemical Society, 1948, 68:522.
Ashley et al., "A Catalytic Antibody Model for PLP-Dependent Decarboxylases," Journal of the American Chemical Society, 1993, 115:2515-2516.
Doering et al., "Mechanism of the Decarboxylation of alpha-Pyridylacetic Acid," Journal of the American Chemical Society, Jan. 1950, 72:143-147.
701 Disintegration, USP 35, 2012, 293-295, The United States Pharmacopeial Convention.
Ecenarro, Susana, "Selecting the Final Sodf: A Comparison of Capsules and Tablets," Tablets and Capsules, Jan. 11, 2018, 12 pages, https://www.tabletscapsules.com/3641-Technical- Articles/591767-Selecting-the-final-SODF-A-comparison-of-capsules-and-tablets/.
European Pharmacopoeia 6.0, p. 717-719, Capsules, 2007.
European Pharmacopoeia 6.0, p. 748-750, Tablets, 2007.
JP XVII, Japanese Pharmacopoeia, 17th Edition, Apr. 1, 2016, English Version, General Tests / 9.41, p. 256.
Markl et al., "A Review of Disintegration Mechanism and Measurement," Pharm. Res., 2017, 34:890- 917.
Morais et al., "The New European Medicines Agency Guideline on the Investigation of Bioequivalence," Basic & Clinical Pharmacology & Toxicology, Mar. 2010, 106(3):221-225.
Reddy et al., "In Vitro Dissolution of Generic Immediate-Release Solid Oral Dosage Forms Containing BCS Class I Drugs: Comparative Assessment of Metronidazole, Zidovudine, and Amoxicillin Versus Relevant Comparator Pharmaceutical Products in South Africa and India," AAPS PharmSciTech, Oct. 2014 (online May 22, 2014), 15(5): 1076-1086.
Sun, Changquan Calvin, "Microstructure of Tablet-Pharmaceutical Significance, Assessment, and Engineering," Pharm. Res., 2017, 34:918-928.

* cited by examiner

[Figure 1]
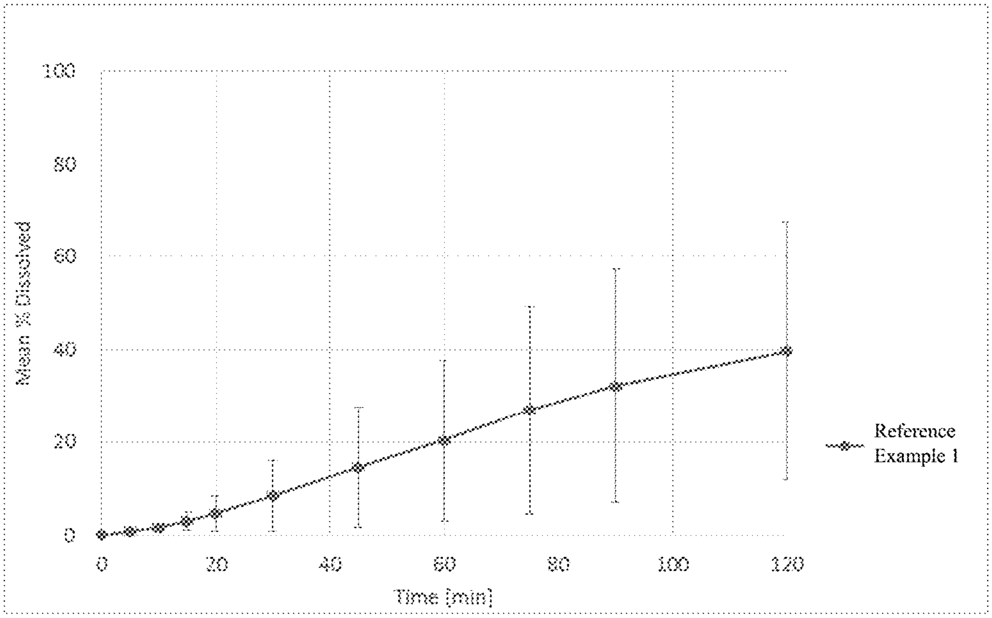
[Figure 2]
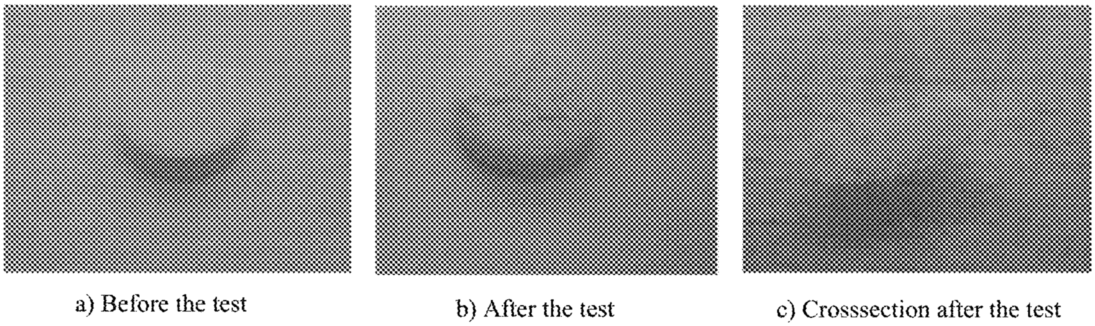
a) Before the test b) After the test c) Crosssection after the test

[Figure 3]
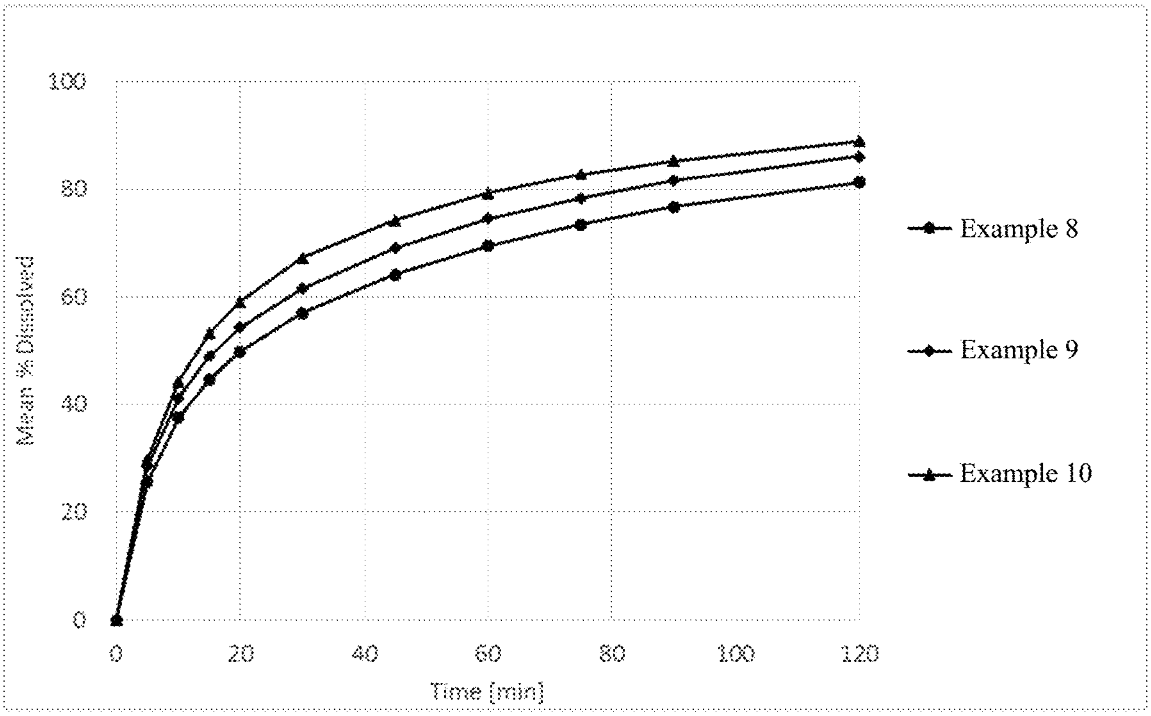
[Figure 4]
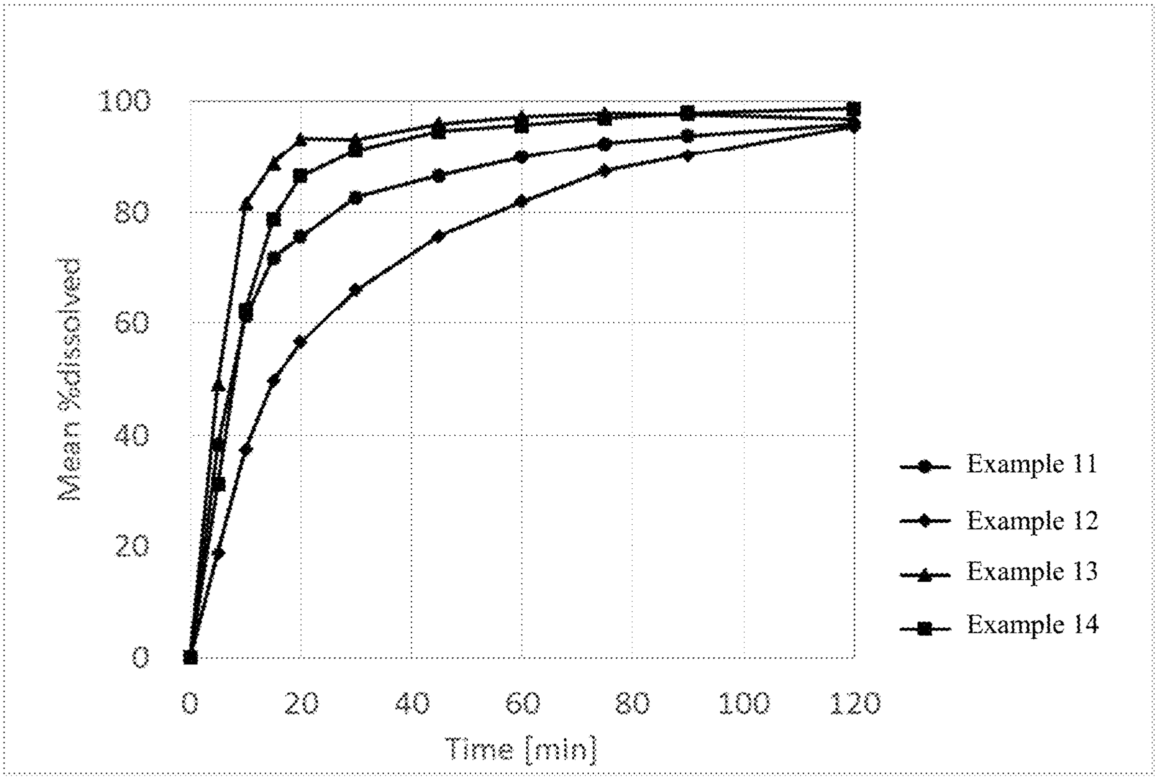

[Figure 5]
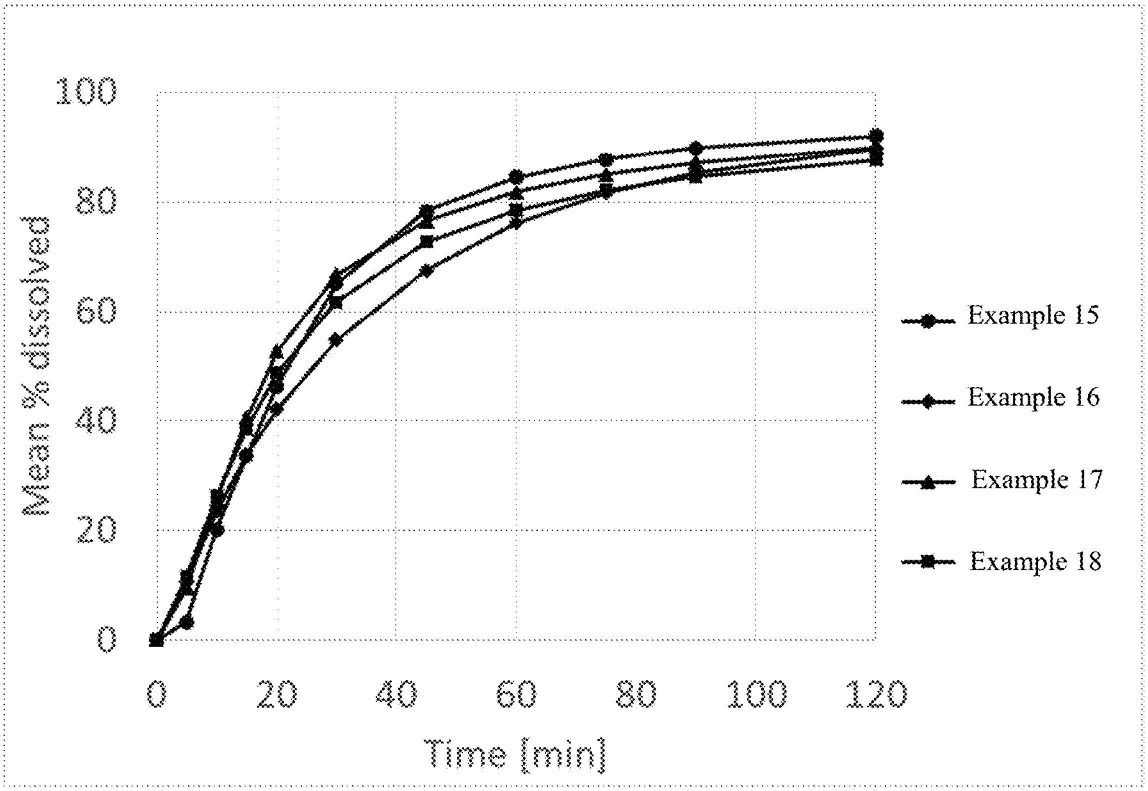

PHARMACEUTICAL COMPOSITION CONTAINING 9-ETHYL-6, 6-DIMETHYL-8-(4-MORPHOLIN-4-YL-PIPERIDIN-1-YL)-11-OXO-6, 11-DIHYDRO-5H-BENZO[B]CARBAZOLE-3-CARBONITRILE

CROSS-REFERENCE TO RELATED APPLICATIONS

This application is the U.S. National Stage of PCT/JP2019/025856, filed Jun. 28, 2019, which claims priority to JP 2018-124830, filed Jun. 29, 2018.

TECHNICAL FIELD

The present invention relates to a pharmaceutical composition that is suitable for a high-dose formulation of a poorly soluble basic agent, particularly a compound represented by formula (I), and a high dose tablet thereof.

BACKGROUND ART

Anaplastic Lymphoma Kinase (ALK) is one of receptor tyrosine kinases belonging to the insulin receptor family (Non-Patent Literature 1 and Non-Patent Literature 2). ALK gene alteration has been reported cause production of an abnormal kinase which is fused with another gene.

Diseases associated with ALK abnormality include, for example, cancer and cancer metastasis (Non-Patent Literature 1 and Patent Literature 1), depression, and cognitive impairment (Non-Patent Literature 2). ALK inhibitors will provide effective therapeutic and prophylactic drugs for these diseases.

As compounds having an effect of inhibiting ALK, a compound represented by formula (I) (compound name: 9-ethyl-6,6-dimethyl-8-(4-morpholin-4-yl-piperidin-1-yl)-11-oxo-6,11-dihydro-5H-benzo[b]carbazole-3-carbonitrile)

[Formula 1]

(I)

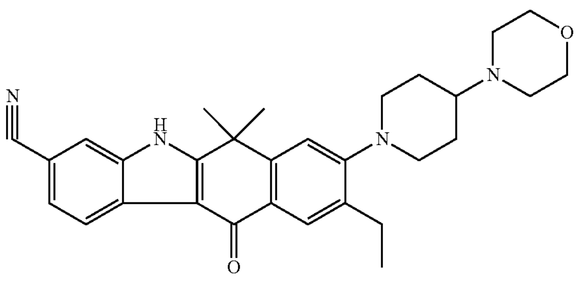

and the like are known (Patent Literature 2, Patent Literature 3, Patent Literature 4 and Patent Literature 5).

The compound represented by formula (I) is a poorly soluble basic agent and has been reported to be formulated by preparing a composition comprising the compound in combination with a dissolution aid (Patent Literature 3) or by forming granules comprising the compound represented by formula (I) or a salt thereof and combining the granules with a disintegrator to provide capsules with good dissolution (Patent Literature 5).

A pharmaceutical formulation comprising, as an active ingredient, a poorly soluble basic agent such as the compound represented by formula (I) typically has low absorption when orally administered. Accordingly, a high-dose formulation is usually used to increase absorption and improve oral absorbability of the active ingredient. However, when a drug insoluble or poorly soluble in water is compressed to form tablets at a high dose, the poor solubility or insolubility of the drug tends to become stronger due to its property, resulting in problems in the dissolution and oral absorbability.

CITATION LIST

Patent Literature

[Patent Literature 1] Japanese Patent Laid-Open No. 2009-100783
[Patent Literature 2] Japanese Patent No. 4588121
[Patent Literature 3] Japanese Patent No. 4918630
[Patent Literature 4] Japanese Patent No. 5006987
[Patent Literature 5] Japanese Patent No. 5859712

Non-Patent Literature

[Non-Patent Literature 1] Nature, Vol. 448, p. 561-566, 2007
[Non-Patent Literature 2] Neuropsychopharmacology, Vol. 33, p. 685-700, 2008

SUMMARY OF INVENTION

Technical Problem

To improve absorbability of a pharmaceutical composition comprising a poorly soluble basic agent, particularly the compound represented by formula (I) or a salt thereof, there are demands for high-dose formulations with excellent disintegration and dissolution.

Solution to Problem

Under such circumstances, the present inventors conducted intensive studies to solve the problem and found that by adding a basic substance to a poorly soluble basic agent, particularly the compound represented by formula (I) or a salt thereof to prepare a pharmaceutical composition, a high-dose tablet can be obtained, in which formation of an impermeable film upon disintegration of the tablet formed from the composition is prevented and which has good dissolution.

More specifically, the present invention is as follows:

(1) A pharmaceutical composition comprising a compound represented by formula (I) or a salt thereof, a surfactant, and a basic substance.

[Formula 2]

(I)

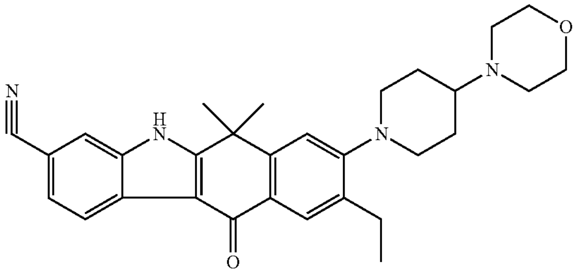

(2) The composition according to (1), wherein the surfactant is an anionic surfactant.

(3) The composition according to (2), wherein the anionic surfactant is sodium lauryl sulfate.

(4) The composition according to any of (1) to (3), further comprising a disintegrator.

(5-1) The composition according to any of (1) to (4), wherein a weight ratio of the compound represented by formula (I) or a salt thereof to the surfactant ranges from 100:3 to 100:50.

(5-2) The composition according to any of (1) to (4), wherein a weight ratio of the compound represented by formula (I) or a salt thereof to the surfactant ranges from 100:12.5 to 100:25.

(5-3) The composition according to any of (1) to (4), wherein a weight ratio of the compound represented by formula (I) or a salt thereof to the surfactant is 100:25.

(6-1) The composition according to (4) or (5), wherein the disintegrator is contained in an amount of 5 wt % or more.

(6-2) The composition according to (4) or (5), wherein the disintegrator is contained in an amount of 7.5 wt % or more.

(6-3) The composition according to (4) or (5), wherein the disintegrator is contained in an amount of 8.5 wt % or more.

(6-4) The composition according to (4) or (5), wherein the disintegrator is contained in an amount of 10 wt % or more.

(7-1) The composition according to any of (4) to (6), wherein the disintegrator is at least one substance selected from the group consisting of sodium starch glycolate, low-substituted hydroxypropylcellulose, carmellose calcium, pregelatinized starch, sodium chloride, corn starch, croscarmellose sodium, crystalline cellulose, silicic anhydride, and carmellose.

(7-2) The composition according to any of (4) to (6), wherein the disintegrator is at least one substance selected from the group consisting of carmellose calcium, crospovidone, sodium starch glycolate, and croscarmellose sodium.

(7-3) The composition according to any of (4) to (6), wherein the disintegrator is carmellose calcium.

(8) The composition according to any of (1) to (7), wherein the basic substance is at least one substance selected from the group consisting of an inorganic basic substance and an organic basic substance.

(9-1) The composition according to any of (1) to (8), wherein the basic substance is at least one substance selected from the group consisting of L-tryptophan, L-lysine, magnesium hydroxide, magnesium silicate, calcium bicarbonate, sodium bicarbonate, magnesium aluminometasilicate, L-arginine, meglumine, magnesium oxide, and magnesium carbonate.

(9-2) The composition according to any of (1) to (8), wherein the basic substance is at least one substance selected from the group consisting of magnesium aluminometasilicate, L-arginine, meglumine, magnesium oxide, magnesium hydroxide, and magnesium carbonate.

(9-3) The composition according to any of (1) to (8), wherein the basic substance is at least one substance selected from the group consisting of magnesium aluminometasilicate, magnesium oxide, and magnesium carbonate.

(9-4) The composition according to any of (1) to (8), wherein the basic substance is magnesium aluminometasilicate.

(9-5) The composition according to any of (1) to (8), wherein the magnesium aluminometasilicate is at least one substance selected from the group consisting of Neusilin(R) US2, S2, UFL2, FH2, and NS2N (Fuji Chemical Industries Co., Ltd.), and PTU-F (Tomita Pharmaceutical Co., Ltd.).

(9-6) The composition according to any of (1) to (8), wherein the magnesium aluminometasilicate is Neusilin(R) US2 or S2 (Fuji Chemical Industries Co., Ltd.).

(10-1) The composition according to any of (1) to (9), wherein the basic substance is contained in an amount of 5 wt % or more.

(10-2) The composition according to any of (1) to (9), wherein the basic substance is contained in an amount of 5 wt % or more and 30 wt % or less.

(10-3) The composition according to any of (1) to (9), wherein the basic substance is contained in an amount of 7.5 wt % or more.

(10-4) The composition according to any of (1) to (9), wherein the basic substance is contained in an amount of 7.5 wt % or more and 30 wt % or less.

(10-5) The composition according to any of (1) to (9), wherein a weight ratio of the compound represented by formula (I) or a salt thereof to the basic substance ranges from 100:5 to 100:60 in terms of the free form.

(10-6) The composition according to any of (1) to (9), wherein a weight ratio of the compound represented by formula (I) or a salt thereof to the basic substance ranges from 100:10 to 100:50 in terms of the free form.

(10-7) The composition according to any of (1) to (9), wherein a weight ratio of the compound represented by formula (I) or a salt thereof to the basic substance ranges from 100:20 to 100:40 in terms of the free form.

(10-8) The composition according to any of (1) to (9), wherein the compound represented by formula (I) or a salt thereof is contained in an amount of 20 to 70 wt % in terms of the free form based on the total amount of the composition.

(10-9) The composition according to any of (1) to (9), wherein the compound represented by formula (I) or a salt thereof is contained in an amount of 35 to 60 wt % in terms of the free form based on the total amount of the composition.

(10-10) The composition according to any of (1) to (9), wherein the compound represented by formula (I) or a salt thereof is contained in an amount of 45 to 50 wt % in terms of the free form based on the total amount of the composition.

(11) A tablet comprising the composition according to any of (1) to (10).

(12-1) The tablet according to any of (1) to (11), wherein the compound represented by formula (I) or a salt thereof is contained in an amount of 150 mg to 800 mg per unit formulation in terms of the free form.

(12-2) The tablet according to any of (1) to (11), wherein the compound represented by formula (I) or a salt thereof is contained in an amount of 150 mg to 400 mg per unit formulation in terms of the free form.

(12-3) The tablet according to any of (1) to (11), wherein the compound represented by formula (I) or a salt thereof is contained in an amount of 200 mg to 300 mg per unit formulation in terms of the free form.

(13-1) The tablet according to (11) or (12), wherein a dissolution rate at 30 minutes is 45% or more as measured in the paddle method for dissolution test specified in the Japanese Pharmacopeia, using the 1st fluid for dissolution test specified in the Japanese Pharmacopeia containing polyoxyethylene (10) octylphenyl ether (4%).

(13-2) The tablet according to (11) or (12), wherein a dissolution rate at 30 minutes is 60% or more as measured in the paddle method for dissolution test specified in the Japanese Pharmacopeia, using the 1st fluid for dissolution test specified in the Japanese Pharmacopeia containing polyoxyethylene (10) octylphenyl ether (4%).

(13-3) The tablet according to (11) or (12), wherein a dissolution rate at 30 minutes is 75% or more as measured in the paddle method for dissolution test specified in the Japanese Pharmacopeia, using the 1st fluid for dissolution test specified in the Japanese Pharmacopeia containing polyoxyethylene (10) octylphenyl ether (4%).

(13-4) The tablet according to (11) or (12), a dissolution rate at 75 minutes is 70% or more as measured in the paddle method for dissolution test specified in the Japanese Pharmacopeia, using the 1st fluid for dissolution test specified in the Japanese Pharmacopeia containing polyoxyethylene (10) octylphenyl ether (4%).

(13-5) The tablet according to (11) or (12), wherein a dissolution rate at 30 minutes is 45% or more as measured in the paddle method for dissolution test specified in the Japanese Pharmacopeia, using purified water (900 mL) containing formic acid (33 mL) and polyoxyethylene (10) octylphenyl ether (2%).

(13-6) The tablet according to (11) or (12), wherein a dissolution rate at 30 minutes is 60% or more as measured in the paddle method for dissolution test specified in the Japanese Pharmacopeia, using purified water (900 mL) containing formic acid (33 mL) and polyoxyethylene (10) octylphenyl ether (2%).

(13-7) The tablet according to (11) or (12), wherein a dissolution rate at 30 minutes is 75% or more as measured in the paddle method for dissolution test specified in the Japanese Pharmacopeia, using purified water (900 mL) containing formic acid (33 mL) and polyoxyethylene (10) octylphenyl ether (2%).

(13-8) The tablet according to (11) or (12), wherein a dissolution rate at 75 minutes is 70% or more as measured in the paddle method for dissolution test specified in the Japanese Pharmacopeia, using purified water (900 mL) containing formic acid (33 mL) and polyoxyethylene (10) octylphenyl ether (2%).

(13-9) The tablet according to (11) or (12), wherein a residue of a sample is observed, but the residue is a minor amount of a soft substance or a muddy substance at 30 minutes in the disintegration test specified in the Japanese Pharmacopeia using water as a test medium.

(13-10) The tablet according to (11) or (12), wherein no residue of a sample is observed at 30 minutes in the disintegration test specified in the Japanese Pharmacopeia using water as a test medium.

(13-11) The tablet according to (11) or (12), wherein a residue of a sample is observed, but the residue is a minor amount of a soft substance or a muddy substance at 30 minutes in the disintegration test specified in the Japanese Pharmacopeia using, as a test medium, the 1st fluid for dissolution test specified in the Japanese Pharmacopeia.

(13-12) The tablet according to (11) or (12), wherein no residue of a sample is observed at 30 minutes in the disintegration test specified in the Japanese Pharmacopeia using, as a test medium, the 1st fluid for dissolution test specified in the Japanese Pharmacopeia.

(14) A pharmaceutical composition comprising a compound represented by formula (I) or a salt thereof; at least one basic substance selected from the group consisting of L-tryptophan, L-lysine, magnesium hydroxide, magnesium silicate, calcium bicarbonate, magnesium aluminometasilicate, L-arginine, meglumine, magnesium oxide, and magnesium carbonate; carmellose calcium; hydroxypropylcellulose; sodium lauryl sulfate; and magnesium stearate.

(14-1) A pharmaceutical composition comprising a compound represented by formula (I) or a salt thereof; at least one basic substance selected from the group consisting of L-tryptophan, L-lysine, magnesium hydroxide, magnesium silicate, calcium bicarbonate, magnesium aluminometasilicate, L-arginine, meglumine, magnesium oxide, and magnesium carbonate; carmellose calcium; D-mannitol; and sodium lauryl sulfate.

(14-2) A pharmaceutical composition comprising a compound represented by formula (I) or a salt thereof; at least one basic substance selected from the group consisting of L-tryptophan, L-lysine, magnesium hydroxide, magnesium silicate, calcium bicarbonate, magnesium aluminometasilicate, L-arginine, meglumine, magnesium oxide, and magnesium carbonate; crospovidone; lactose hydrate; and sodium lauryl sulfate.

(14-3) A pharmaceutical composition comprising a compound represented by formula (I) or a salt thereof; at least one basic substance selected from the group consisting of L-tryptophan, L-lysine, magnesium hydroxide, magnesium silicate, calcium bicarbonate, magnesium aluminometasilicate, L-arginine, meglumine, magnesium oxide, and magnesium carbonate; carmellose calcium; D-mannitol; sodium lauryl sulfate; hydroxypropylcellulose; and magnesium stearate.

(14-4) A pharmaceutical composition comprising a compound represented by formula (I) or a salt thereof; at least one basic substance selected from the group consisting of L-tryptophan, L-lysine, magnesium hydroxide, magnesium silicate, calcium bicarbonate, magnesium aluminometasilicate, L-arginine, meglumine, magnesium oxide, and magnesium carbonate; crospovidone; lactose hydrate; sodium lauryl sulfate; hydroxypropylcellulose; and magnesium stearate.

(15) A tablet comprising the composition according to (14).

(16-1) The tablet according to (15), wherein the compound represented by formula (I) or a salt thereof is contained in an amount of 150 mg to 800 mg per unit formulation in terms of the free form.

(16-2) The tablet according to (15), wherein the compound represented by formula (I) or a salt thereof is contained in an amount of 150 mg to 600 mg per unit formulation in terms of the free form.

(16-3) The tablet according to (15), wherein the compound represented by formula (I) or a salt thereof is contained in an amount of 200 mg to 300 mg per unit formulation in terms of the free form.

(17-1) The tablet according to (15) or (16), wherein a dissolution rate at 30 minutes is 45% or more as measured in the paddle method for dissolution test specified in the Japanese Pharmacopeia, using the 1st fluid for dissolution test specified in the Japanese Pharmacopeia containing polyoxyethylene (10) octylphenyl ether (4%).

(17-2) The tablet according to (15) or (16), wherein a dissolution rate at 30 minutes is 60% or more as measured in the paddle method for dissolution test specified in the Japanese Pharmacopeia, using the 1st fluid for dissolution test specified in the Japanese Pharmacopeia containing polyoxyethylene (10) octylphenyl ether (4%).

(17-3) The tablet according to (15) or (16), wherein a dissolution rate at 30 minutes is 75% or more as measured in the paddle method for dissolution test specified in the Japanese Pharmacopeia, using the 1st fluid for dissolution test specified in the Japanese Pharmacopeia containing polyoxyethylene (10) octylphenyl ether (4%).

(17-4) The tablet according to (15) or (16), wherein a dissolution rate at 75 minutes is 70% or more as measured in the paddle method for dissolution test specified in the Japanese Pharmacopeia, using the 1st fluid for dissolution test specified in the Japanese Pharmacopeia containing polyoxyethylene (10) octylphenyl ether (4%).

(17-5) The tablet according to (15) or (16), wherein a dissolution rate at 30 minutes is 45% or more as measured in the paddle method for dissolution test specified in the Japanese Pharmacopeia using purified water (900 mL) containing formic acid (33 mL) and polyoxyethylene (10) octylphenyl ether (2%).

(17-6) The tablet according to (15) or (16), wherein a dissolution rate at 30 minutes is 60% or more as measured in the paddle method for dissolution test specified in the Japanese Pharmacopeia, using purified water (900 mL) containing formic acid (33 mL) and polyoxyethylene (10) octylphenyl ether (2%).

(17-7) The tablet according to (15) or (16), wherein a dissolution rate at 30 minutes is 75% or more as measured in the paddle method for dissolution test specified in the Japanese Pharmacopeia, using purified water (900 mL) containing formic acid (33 mL) and polyoxyethylene (10) octylphenyl ether (2%).

(17-8) The tablet according to (15) or (16), wherein a dissolution rate at 75 minutes is 70% or more as measured in the paddle method for dissolution test specified in the Japanese Pharmacopeia, using purified water (900 mL) containing formic acid (33 mL) and polyoxyethylene (10) octylphenyl ether (2%).

(17-9) The tablet according to (15) or (16), wherein a residue of a sample is observed, but the residue is a minor amount of a soft substance or a muddy substance at 30 minutes in the disintegration test specified in the Japanese Pharmacopeia using water as a test medium.

(17-10) The tablet according to (15) or (16), wherein no residue of a sample is observed at 30 minutes in the disintegration test specified in the Japanese Pharmacopeia using water as a test medium.

(17-11) The tablet according to (15) or (16), wherein a residue of a sample is observed, but the residue is a minor amount of a soft substance or a muddy substance at 30 minutes in the disintegration test specified in the Japanese Pharmacopeia using, as a test medium, the 1st fluid for dissolution test specified in the Japanese Pharmacopeia.

(17-12) The tablet according to (15) or (16), wherein no residue of a sample is observed at 30 minutes in the disintegration test specified in the Japanese Pharmacopeia using, as a test medium, the 1st fluid for dissolution test specified in the Japanese Pharmacopeia.

(18) The tablet according to (15) or (16), wherein a dissolution rate is 45% or more at 30 minutes and/or 75% or more at 70 minutes in the dissolution test by the paddle method performed at 100 rotations/minute using a test medium containing polyoxyethylene (10) octylphenyl ether (4%) prepared in a solution having about pH 1.2 and containing sodium chloride (2.0 g) dissolved in hydrochloric acid (7.0 ml) and water (q.s. to 1000 mL).

Advantageous Effects of Invention

The composition of the present invention can provide high-dose formulations with good dissolution and disintegration, which prevent formation of an impermeable film in the disintegration of tablets formed from the compositions and contain, as an active ingredient, a poorly soluble basic agent, particularly a compound represented by formula (I) or a salt thereof. The composition of the present invention also allows formulation into a high-dose formulation with good dissolution profiles, resulting in a reduction of dosing frequency of the formulation and thus an improvement of drug compliance.

The pharmaceutical composition of the present invention is formulated into high-dose tablets with good dissolution, regardless of the presence or absence of formation of granules, when tableted.

BRIEF DESCRIPTION OF DRAWINGS

FIG. 1 shows a dissolution profile of a tablet of Reference Example 1.

FIG. 2 shows photographs of a) an appearance before the test, b) an appearance after the test, and c) a midsection after the test of the tablet of Reference Example 1.

FIG. 3 shows dissolution profiles of Examples 8 to 10.

FIG. 4 shows dissolution profiles of Examples 11 to 14.

FIG. 5 shows dissolution profiles of Examples 15 to 18.

DESCRIPTION OF EMBODIMENTS

The present invention will be described in detail below.

As used herein, the term "pharmaceutical composition" refers to a mixture comprising two or more substances that is used for treating and preventing diseases. According to an aspect of the present invention, the pharmaceutical composition is used for production of a pharmaceutical formulation. The term "pharmaceutical formulation" refers to a formulation for treating and preventing diseases, and preferably an oral administration formulation in the present invention. The term "oral administration formulation" refers to a formulation that can be orally administered and comprises an active ingredient mainly absorbed in the intestinal tract.

The oral administration formulation includes a solid formulation and a liquid formulation, with a solid formulation being preferable in the present invention. The solid formulation specifically includes a tablet, a capsule, a solution, a powder, a troche, a chewable tablet, a granule, a gel, and a film, with a tablet being preferable.

In the present invention, granules may or may not be used when tablets are produced. When granules are used for production of tablets, granules may have a mean particle diameter used in typical formulation.

The term “compound represented by formula (I)” refers to a compound represented by formula (I):

[Formula 3]

(I)

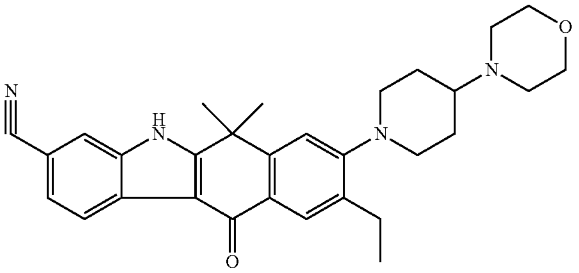

having a compound name of 9-ethyl-6,6-dimethyl-8-(4-morpholin-4-yl-piperidin-1-yl)-11-oxo-6,11-dihydro-5H-benzo[b]carbazole-3-carbonitrile.

A “salt” of the compound represented by formula (I) is preferably a pharmaceutically acceptable salt. The “pharmaceutically acceptable salt” includes, for example, hydrochlorides; hydrobromides; hydroiodides; phosphates; phosphonates; sulfates; sulfonates including methanesulfonates and p-toluenesulfonates; carboxylates including acetates, citrates, malates, tartrates, succinates, and salicylates; or alkaline metal salts including sodium salts and potassium salts; alkaline-earth metal salts including magnesium salts and calcium salts; and ammonium salts including ammonium salts, alkylammonium salts, dialkylammonium salts, trialkylammonium salts, and tetraalkylammonium salts.

The pharmaceutically acceptable salt is preferably a hydrochloride, and most preferably a monohydrochloride.

The compound represented by formula (I) or a salt thereof can be produced using any known method (e.g., the methods described in Patent Literature 2).

A monohydrochloride of the compound represented by formula (I) may be amorphous or crystalline. When the monohydrochloride is crystalline, a crystal having peaks present at diffraction angles (2θ) of about 8.4°, 14.0°, 16.7°, 18.8°, and 23.3° in the powder X-ray diffraction pattern is preferable. An amorphous monohydrochloride of the compound represented by formula (I) can be produced using the method described in WO 2016/021707, and a crystalline monohydrochloride of the compound having these peaks can be produced using the method described in WO 2015/163447.

The compound represented by formula (I) or a salt thereof is contained in an amount of 20 to 70 wt %, preferably 35 to 60 wt %, and more preferably 45 to 50 wt % in terms of the free form, based on the total amount of the composition.

A formulations obtained from the composition of the present invention contains the compound represented by formula (I) or a salt thereof in an amount of 150 mg to 800 mg, preferably 150 mg to 400 mg, and particularly preferably, 200 mg to 300 mg per unit formulation in terms of the free form.

The term “surfactant” refers to a substance having both a hydrophilic group and a hydrophobic group in a molecule. The surfactant includes an ionic surfactant and a nonionic surfactant.

The ionic surfactant means ionic surfactants that ionize into ions (charged atoms or atomic groups) when dissolved in water. The ionic surfactant is further classified into an anionic surfactant, a cationic surfactant, and an amphoteric surfactant depending on the charge of the ion to be produced.

Examples of the nonionic surfactant include sugar ester surfactants such as a sorbitan fatty acid ester (C12-18), a POE sorbitan fatty acid ester (C12-18), and a sucrose fatty acid ester; fatty acid ester type such as a POE fatty acid ester (C12-18), a POE resin acid ester, and a POE fatty acid diester (C12-18); alcohol-based type such as a POE alkyl ether (C12-18); alkyl phenol surfactants such as a POE alkyl (C8-12) phenyl ether, a POE dialkyl (C8-12) phenyl ether, and a POE alkyl (C8-12) phenyl ether formalin condensate; polyoxyethylene-polyoxypropylene block polymer surfactants such as a polyoxyethylene-polyoxypropylene block polymer and an alkyl (C12-18) polyoxyethylene-polyoxypropylene block polymer ether; alkylamine type such as a POE alkylamine (C12-18) and a POE fatty acid amide (C12-18); bisphenol surfactants such as a POE fatty acid bisphenyl ether; polycyclic aromatic surfactants such as a POA benzylphenyl (or phenylphenyl) ether and a POA styrylphenyl (or phenylphenyl) ether; POE ether and ester type silicon and fluorine-based surfactants; and vegetable oil surfactants such as POE castor oil and POE hydrogenated castor oil. Examples of the nonionic surfactant preferably include polyoxyl 40 stearate, sorbitan trioleate, polyoxyethylene (105) polyoxypropylene (5) glycol, polyoxyethylene hydrogenated castor oil 60, polyoxyl 35 castor oil, and lauromacrogol.

Examples of the anionic surfactant include sulfate surfactants such as an alkyl sulfate (C12-18, Na, NH4, alkanolamine), a POE alkyl ether sulfate (C12-18, Na, NH4, alkanolamine), a POE alkyl phenyl ether sulfate (C12-18, NH4, alkanolamine, Ca), a POE benzyl (or styryl) phenyl (or phenylphenyl) ether sulfate (Na, NH4, alkanolamine), a polyoxyethylene, and a polyoxypropylene block polymer sulfate (Na, NH4, alkanolamine); sulfonate surfactants such as a paraffin (alkane) sulfonate (C12-22, Na, Ca, alkanolamine), an AOS (C14-16, Na, alkanolamine), a dialkyl sulfosuccinate (C8-12, Na, Ca, Mg), an alkylbenzene sulfonate (C12, Na, Ca, Mg, NH4, alkylamine, alkanol, amine, cyclohexylamine), a mono or dialkyl (C3-6) naphthalene sulfonate (Na, NH4, alkanolamine, Ca, Mg), a naphthalene sulfonate-formalin condensate (Na, NH4), an alkyl (C8-12) diphenyl ether disulfonate (Na, NH4), a lignin sulfonate (Na, Ca), a POE alkyl (C8-12) phenyl ether sulfonate (Na), and a POE alkyl (C12-18) ether sulfosuccinic acid half ester (Na); carboxylate surfactants such as a fatty acid salt (C12-18, Na, K, NH4, alkanolamine), an N-methyl-fatty acid sarcosinate (C12-18, Na) and a resinate (Na, K); and phosphate surfactants such as a POE alkyl (C12-18) ether phosphate (Na, alkanolamine), a POE mono or dialkyl (C8-12) phenyl ether phosphate (Na, alkanolamine), a POE benzylated (or styrylated) phenyl (or phenylphenyl) ether phosphate (Na, alkanolamine), a polyoxyethylene-polyoxypropylene block polymer (Na, alkanolamine), a phosphatidylcholine-phosphatidyl ethanol imine (lecithin), and an alkyl (C8-12) phosphate. Examples of the anionic surfactant preferably include monoalkyl sulfates such as sodium lauryl sulfate, sodium tetradecyl sulfate, sodium hexadecyl sulfate, and sodium octadecyl sulfate; dioctylsodium sulfosuccinate; sodium lauroyl sarcosinate; and sodium dodecylbenzenesulfonate.

In the present invention, the surfactants may be used in combination of two or more in an appropriate ratio.

In the present invention, the surfactant is preferably an anionic surfactant.

Preferable surfactants are selected from the group consisting of a monoalkyl sulfate, polyoxyl 40 stearate, sorbitan trioleate, polyoxyethylene (105) polyoxypropylene (5) glycol, polyoxyethylene hydrogenated castor oil 60, polyoxyl 35 castor oil, lauromacrogol, dioctylsodium sulfosuccinate, lauroylsarcosine sodium, sodium dodecylbenzenesulfonate, and a mixture thereof.

More preferable surfactants are selected from the group consisting of a monoalkyl sulfate, sorbitan trioleate, polyoxyethylene (105) polyoxypropylene (5) glycol, polyoxyethylene hydrogenated castor oil 60, polyoxyl 35 castor oil, dioctylsodium sulfosuccinate, lauroylsarcosine sodium, sodium dodecylbenzenesulfonate, and a mixture thereof.

Even more preferable surfactants are selected from the group consisting of sodium lauryl sulfate, sodium tetradecyl sulfate, sodium hexadecyl sulfate, sodium octadecyl sulfate, and a mixture thereof.

A particularly preferable surfactant is a mixture of sodium lauryl sulfate and polyoxyethylene (105) polyoxypropylene (5) glycol.

The most preferable surfactant is sodium lauryl sulfate.

In the present invention, the ionic surfactant is more preferably sodium lauryl sulfate.

When sodium lauryl sulfate is used in the present invention, a crystal obtained by spray drying or crystallization can be used. It should be noted that sodium lauryl sulfate is known to have crystal polymorphs including a monohydrate, a ½ hydrate, a ⅛ hydrate, and a non-solvate (Journal of Crystal Growth 263 (2004) 480-490). Any of the crystal polymorphs can be used in the composition or formulation of the present invention.

The surfactant is contained in an amount of 5 wt % or more, preferably 5 wt % or more and 30 wt % or less, more preferably of 7.5 wt % or more, and most preferably 7.5 wt % or more and 30 wt % or less, based on the total amount of the composition.

A weight ratio of the compound represented by formula (I) or a salt thereof to the surfactant contained in the composition or formulation of the present invention preferably ranges from 100:3 to 100:50, more preferably 100:12.5 to 100:25, and most preferably 100:25.

The term "basic substance" refers to a substance that is defined as a base according to preferably Lewis's definition and more preferably Bronsted-Lowry's definition. The basic substance may be any known pharmacologically acceptable basic substance and is not limited to particular basic substances. The basic substance may be an inorganic basic substance or an organic basic substance. The basic substance may be used alone or in combination of two or more.

Examples of the inorganic basic substance include metal oxides such as magnesium oxide, calcium oxide, and aluminum oxide; metal hydroxides such as sodium hydroxide, potassium hydroxide, magnesium hydroxide, calcium hydroxide, and aluminum hydroxide; metal carbonates such as sodium carbonate, potassium carbonate, magnesium carbonate, and calcium carbonate; metal bicarbonates such as sodium bicarbonate and potassium bicarbonate; metal phosphates such as trisodium phosphate, tripotassium phosphate, tricalcium phosphate, trimagnesium phosphate, sodium pyrophosphate, potassium pyrophosphate, sodium polyphosphate, and potassium polyphosphate; metal hydrogen phosphates such as sodium hydrogen phosphate and potassium hydrogen phosphate; metal silicates such as sodium silicate, magnesium silicate, calcium silicate, synthetic aluminum silicate, synthetic sodium magnesium silicate, and talc; complex aluminum silicate compounds such as magnesium aluminosilicate, aluminum magnesium silicate, and magnesium aluminometasilicate; complex aluminum-magnesium compounds such as synthetic hydrotalcite; and inorganic ammonium salts such as ammonium hydroxide, ammonium carbonate, ammonium hydrogen carbonate, and ammonium hydrogen phosphate.

Examples of the organic basic substance include metal salts of organic acids, organic amines, and basic amino acids.

Examples of the metal salts of organic acids include a sodium salt, a potassium salt, a magnesium salt, and a calcium salt of organic acids such as citric acid, succinic acid, tartaric acid, fumaric acid, maleic acid, malonic acid, and malic acid.

Examples of the organic amines include meglumine, monoethanolamine, diisopropanolamine, triethanolamine, monoisopropanolamine, diisopropanolamine, triisopropanol amine, 2-amino-2-methyl-1-propanol, 2-amino-2-methyl-1,3-propanediol, and polyoxyethylene alkyl amine.

Examples of the basic amino acids include lysine, arginine, phenylalanine, tyrosine, histidine, proline, oxyproline, ornithine, hydroxylysine, and a derivative thereof.

Examples of the basic substance preferably include metal oxides such as magnesium oxide, calcium oxide, and aluminum oxide; metal hydroxides such as sodium hydroxide, potassium hydroxide, magnesium hydroxide, calcium hydroxide, and aluminum hydroxide; metal carbonates such as sodium carbonate, potassium carbonate, magnesium carbonate, and calcium carbonate; metal bicarbonates such as sodium bicarbonate and potassium bicarbonate; metal phosphates such as trisodium phosphate, tripotassium phosphate, tricalcium phosphate, trimagnesium phosphate, sodium pyrophosphate, potassium pyrophosphate, sodium polyphosphate, and potassium polyphosphate; metal hydrogen phosphates such as sodium hydrogen phosphate and potassium hydrogen phosphate; metal silicates such as sodium silicate, magnesium silicate, calcium silicate, synthetic aluminum silicate, synthetic sodium magnesium silicate, and talc; complex aluminum silicate compounds such as magnesium aluminosilicate, aluminum magnesium silicate, and magnesium aluminometasilicate; complex aluminum-magnesium compounds such as synthetic hydrotalcite; and inorganic ammonium salts such as ammonium hydroxide, ammonium carbonate, ammonium hydrogen carbonate, and ammonium hydrogen phosphate.

Alternatively, examples of the basic substance include glycine, L-serine, L-cystine, L-tryptophan, L-proline, L-aspartic acid, L-lysine, L-histidine, L-arginine, L-lysine hydrochloride, meglumine, magnesium aluminometasilicate, magnesium aluminometasilicate, magnesium oxide, magnesium hydroxide, magnesium carbonate, magnesium silicate, and calcium bicarbonate. Examples of the basic substance preferably include L-tryptophan, L-lysine, magnesium hydroxide, magnesium silicate, calcium bicarbonate, sodium bicarbonate, magnesium aluminometasilicate, L-arginine, meglumine, magnesium oxide, and magnesium carbonate; more preferably include magnesium aluminometasilicate, L-arginine, meglumine, magnesium oxide, magnesium hydroxide, magnesium carbonate, and sodium bicarbonate; even more preferably include magnesium aluminometasilicate, magnesium oxide, and magnesium carbonate; and most preferably include magnesium aluminometasilicate.

The magnesium aluminometasilicate is preferably Neusilin(R) US2, S2, UFL2, FH2, or NS2N (Fuji Chemical Industries Co., Ltd.) or PTU-F (Tomita Pharmaceutical Co., Ltd.). More preferably, the magnesium aluminometasilicate is Neusilin(R) US2 or S2 (Fuji Chemical Industries Co., Ltd.).

The basic substance is preferably selected from the group consisting of L-tryptophan, L-lysine, magnesium hydroxide, magnesium silicate, calcium bicarbonate, sodium bicarbonate, magnesium aluminometasilicate, L-arginine, meglumine, magnesium oxide, and magnesium carbonate, and is most preferably selected from the group consisting of L-tryptophan, L-lysine, magnesium hydroxide, magnesium silicate, calcium bicarbonate, sodium bicarbonate, magnesium aluminometasilicate, L-arginine, meglumine, and magnesium oxide.

The basic substance is contained in an amount of 5 wt % or more, 5 wt % or more and 30 wt % or less, 7.5 wt % or more, 7.5 wt % or more and 30 wt % or less, based on the total amount of the composition.

A weight ratio of the compound represented by formula (I) or a salt thereof to the basic substance preferably ranges from 100:5 to 100:60, more preferably 100:10 to 100:50, and most preferably 100:20 to 100:40 in terms of the free form.

The formulation of the present invention is produced using any well-known methods using additive(s) such as an excipient, a lubricant, a coating agent, a binder, a disintegrator, a stabilizer, a flavoring agent, and a diluent.

Examples of the "excipient" include starches such as corn starch, potato starch, wheat starch, rice starch, partially pregelatinized starch, pregelatinized starch, and porous starch; sugars or sugar alcohols such as lactose hydrate, fructose, glucose, mannitol, and sorbitol; anhydrous dibasic calcium phosphate; crystalline cellulose; precipitated calcium carbonate; and calcium silicate. Examples of preferable excipients include starches such as starch, potato starch, and corn starch; lactose hydrate; crystalline cellulose; and anhydrous dibasic calcium phosphate.

The "disintegrator" in the present invention is a component that facilitates rapid disintegration of a solid formulation after orally taken.

Examples of the disintegrator include sodium starch glycolate, low-substituted hydroxypropylcellulose, carmellose calcium, pregelatinized starch, sodium chloride, corn starch, croscarmellose sodium, crystalline cellulose, silicic anhydride, and carmellose.

The amount of the disintegrator used is, for example, 5 wt % or more, preferably 7.5 wt % or more, more preferably 8.5 wt % or more, and particularly preferably 10 wt % or more based on the total amount of the composition or formulation of the present invention. The upper limit of the amount used includes, but is not particularly limited to, 30 wt %. It should be noted that when the formulation of the present invention has a coating film (e.g., a coated tablet), the amount used is based on the total amount of the components to be covered with the coating film (or the total amount of the components to be put in a capsule, or the total amount of the components covered with a coating).

Examples of the "binder" include polyvinylpyrrolidone, macrogol, and similar compounds as listed for the excipient. Specific examples of the binder include hydroxypropylcellulose, hydroxypropylmethylcellulose, methylcellulose, povidone (polyvinylpyrrolidone), and powdered acacia. The amount of the binder used is preferably 0.1 to 50 parts by weight and more preferably 0.5 to 40 parts by weight per 100 parts by weight of the formulation.

Suitable examples of the "lubricant" include magnesium stearate, calcium stearate, talc, sucrose fatty acid ester, and sodium stearyl fumarate.

Examples of the surfactant or emulsifying agent include polysorbate 80, polyoxyl 40 stearate, and lauromacrogol.

Coloring agents may be any substance that is allowed to be added into pharmaceuticals. Examples of the coloring agents include edible pigments such as Food Yellow No. 5 (sunset yellow, the same as Food Yellow No. 6 in the United States), Food Red No. 2, and Food Blue No. 2; edible lake pigments; and iron sesquioxide.

Examples of the stabilizer include p-hydroxybenzoate esters such as methylparaben and propylparaben; alcohols such as chlorobutanol, benzyl alcohol, and phenylethyl alcohol; benzalkonium chloride; phenols such as phenol and cresol; thimerosal; dehydroacetic acid; and sorbic acid.

Examples of the "flavoring agent" include sweeteners, acidulants, and flavors commonly used "Fluidizers" are used for the purpose of improving fluidity of mixed powders or granules. Representative examples of the fluidizers include light anhydrous silicates such as talc and silicon dioxide, and hydrous silicon dioxide. The light anhydrous silicates may be any substance that contains hydrous silicon dioxide ($SiO2 \cdot nH2O$, wherein n is an integer) as a main component. Specific examples of the light anhydrous silicates include Sylysia 320 (trade name, FUJI SILYSIA CHEMICAL LTD.) and AEROSIL 200 (trade name, NIPPON AEROSIL Co., Ltd.).

Preferable examples of "preservatives" include p-hydroxybenzoate esters, chlorobutanol, benzyl alcohol, phenethyl alcohol, dehydroacetic acid, and sorbic acid.

Preferable examples of antioxidants include sulfites and ascorbic acid.

The additives described above may be used in combinations of two or more in an appropriate ratio.

Examples of the solvent used for producing a solution include ethanol, phenol, chlorocresol, purified water, and distilled water.

The solid formulation of the present invention can be produced by mixing the compound represented by formula (I) with a basic substance and the additive(s) described above and then subjecting the mixture to a general production process, preferably a production process described below, to provide a solid formulation.

1) The compound represented by formula (I) is mixed with a basic substance and additives such as an excipient, a disintegrator, and a lubricant. The mixture is then compression molded to produce a solid formulation of the present invention.
2) The compound represented by formula (I) is mixed with a basic substance and additives such as an excipient and a binder. The mixture is then granulated while adding or spraying a solvent (e.g., purified water, ethanol, or a mixture thereof). To the resulting granulated material is added an appropriate amount of a lubricant and optionally a disintegrator and mixed. The mixture is compression molded to produce a solid formulation of the present invention.
3) The compound represented by formula (I) is mixed with a basic substance and additive(s) such as an excipient. The mixture is then granulated while adding or spraying a liquid obtained by dispersing or dissolving a binder and optionally other additives in a solvent (e.g., purified water, ethanol, or a mixture thereof). To the resulting granulated material is added an appropriate amount of a lubricant and optionally a disintegrator and mixed. The mixture is compression molded to produce a solid formulation of the present invention.

The pharmaceutical composition of the present invention also relates to a pharmaceutical composition comprising (i) the compound represented by formula (I) or a salt thereof and (ii) a basic substance.

An aspect of the pharmaceutical composition of the present invention also relates to a non-granular pharmaceutical composition comprising (i) the compound represented by formula (I) or a salt thereof and (ii) a basic substance.

An aspect of the pharmaceutical composition of the present invention also relates to a pharmaceutical composition comprising (i) granules containing the compound represented by formula (I) or a salt thereof and (ii) an external additive containing a basic substance.

A further aspect of the pharmaceutical composition of the present invention is a pharmaceutical composition comprising (i) granules containing the compound represented by formula (I) or a salt thereof and a surfactant, and (ii) an external additive containing a basic compound and a disintegrator.

A further aspect of the pharmaceutical composition of the present invention is a pharmaceutical composition comprising (i) granules containing the compound represented by formula (I) or a salt thereof, a surfactant, and a disintegrator, and (ii) an external additive containing a basic compound and a disintegrator.

As used herein, the term "granules" refers to grains having almost uniform shape and size and the granules are obtained by granulating a raw material in a form of powder, aggregate, solution, or molten liquid via wet granulation, dry granulation, heat granulation, or other similar techniques. The term "non-granular" refers to a state in which granules are not formed.

In the present invention, granules may contain various additives in addition to the surfactant and the disintegrator described above.

For example, the granules may contain the compound represented by formula (I) or a salt thereof, a disintegrator, a surfactant, an excipient, and a binder. The granules may further contain at least one additive selected from a lubricant, a coating agent, a stabilizing agent, a flavoring agent, and a diluent. The granules can be produced by granulating a composition comprising the compound represented by formula (I) or a salt thereof and optionally additives such as a disintegrator, a surfactant, an excipient, a lubricant, a coating agent, a binder, a stabilizer, a flavoring agent, and a diluent, through typical granulating steps.

The granules may have a mean particle diameter used in typical formulation.

It should be noted that the mean particle diameter is a value obtained by feeding 6 g of a granulated material sample onto the top of the stacked sieves different in mesh size (e.g., 850, 500, 355, 250, 180, 106, 75, 53, and 0 μm), shaking the sieves for 3 minutes, measuring the weights of the granulated materials left on the individual sieves, and calculating a particle size equivalent to 50% cumulative percentage through approximation of logarithmic normal distribution based on the mesh sizes of the sieves and cumulative percentages under the sieves.

As used herein, the term "external additive" and "external additive component" refer to components externally added to granules. The external additive component includes further additives such as a lubricant and a fluidizer in addition to a disintegrator.

The disintegrator may be contained in the granules or external additive component. The disintegrator is preferably selected from sodium starch glycolate, low-substituted hydroxypropylcellulose, carmellose calcium, pregelatinized starch, sodium chloride, corn starch, croscarmellose sodium, crystalline cellulose, silicic anhydride, and carmellose, is more preferably selected from carmellose calcium, crospovidone, sodium starch glycolate, and croscarmellose sodium, and is most preferably carmellose calcium and crospovidone.

When the disintegrator is contained in the granules or external additive component, the disintegrator is selected from sodium starch glycolate, low-substituted hydroxypropylcellulose, carmellose calcium, pregelatinized starch, sodium chloride, corn starch, croscarmellose sodium, crystalline cellulose, silicic anhydride, and carmellose, is preferably selected from carmellose calcium, crospovidone, sodium starch glycolate, and croscarmellose sodium, and is most preferably carmellose calcium or crospovidone.

The granules (i) may contain a basic substance in the granules, in which the pharmaceutical composition may comprise (i) granules containing the compound represented by formula (I) or a salt thereof and a basic substance, and (ii) a surfactant. The basic substance is added more preferably as an external additive component.

The basic substance contained in the granules (i) is a substance exemplified above as a basic substance. The basic substance is preferably selected from an inorganic basic substance, a metal salt of organic acids, an organic amine, and a basic amino acid, is more preferably an inorganic basic substance, and is most preferably magnesium aluminometasilicate.

When a basic substance is contained in the external additive component, the basic substance contained in the external additive component (ii) is a substance exemplified above as a basic substance. The basic substance is preferably selected from an inorganic basic substance, a metal salt of organic acids, an organic amine, and a basic amino acid described above, is more preferably an inorganic basic substance described above, and is most preferably magnesium aluminometasilicate.

The basic substance contained in the granules (i) and the external additive component (ii) is preferably contained in an amount of 5 wt % or more, 5 wt % or more and 30 wt % or less, 7.5 wt % or more, or 7.5 wt % or more and 30 wt % or less, based on the total amount of the formulation.

The pharmaceutical composition of the present invention may comprise dissolution aids such as organic polymers described below, in addition to surfactants.

Examples of the "dissolution aid" include organic polymers. Examples of the "organic polymer" used in the present invention specifically include polysaccharides such as hydroxypropylcellulose (hereinafter also referred to as HPC), hydroxypropylmethylcellulose, methylcellulose, propylene glycol alginate ester, powdered agar, guar gum, zein, and hydroxyethyl methylcellulose; synthetic resins such as carboxy vinyl polymer, polyvinyl alcohol, or vinyl acetate resin, and sodium polystyrene sulfonate; and phosphoproteins such as casein and casein sodium.

Of the organic polymers, a polymer that has a solubility in water of 1 g/100 g or more is called a water-soluble polymer. Specific examples of the water-soluble polymer include hydroxypropylcellulose, hydroxypropylmethylcellulose, methylcellulose, propylene glycol alginate ester, casein sodium, a carboxyvinyl polymer, powdered agar, guar gum, copolyvidone, hydroxyethylmethylcellulose, and a polyvinyl alcohol.

Of the organic polymers, a polymer that can be dissolved under acidic conditions at pH of the gastric juice, 1.2 to 3.5, is called a gastrosoluble polymer, whereas a polymer that can be quickly dissolved at the intestinal pH 6 to 8 is called an enteric polymer. Examples of the gastrosoluble polymer include an aminoalkyl methacrylate copolymer E and a polyvinyl acetal diethylamino acetate. Examples of the enteric polymer include a methacrylic acid copolymer LD (emulsion), methacrylic acid copolymer S, purified shellac, carboxymethylethylcellulose, cellulose acetate phthalate (cellaphate), hydroxypropylmethylcellulose acetate succinate, casein, and zein.

Examples of preferable dissolution aids include casein, casein sodium, powdered skim milk, dioctyl sodium sulfosuccinate, polyoxyl 40 stearate, sorbitan trioleate, polyoxyethylene (105) polyoxypropylene (5) glycol, polyoxyethylene hydrogenated castor oil 60, polyoxyl 35 castor oil, lauromacrogol, lauroylsarcosine sodium, sodium tetradecyl sulfate, sodium hexadecyl sulfate, sodium octadecyl sulfate, sodium methyl sulfate, sodium ethyl sulfate, sodium butyl sulfate, sodium octyl sulfate, sodium decyl sulfate, and sodium dodecylbenzenesulfonate.

The dissolution aid may be granular or may be obtained by spray drying.

Examples of the excipient that can be contained in the granules (i) in the present invention include starches such as corn starch, potato starch, wheat starch, rice starch, partially pregelatinized starch, pregelatinized starch, and porous starch; sugars or sugar alcohols such as lactose hydrate, fructose, glucose, mannitol, and sorbitol; anhydrous dibasic calcium phosphate; crystalline cellulose; precipitated calcium carbonate; and calcium silicate. Examples of preferable excipients include starches such as starch, potato starch, and corn starch; lactose hydrate; crystalline cellulose; and anhydrous dibasic calcium phosphate, with mannitol and lactose hydrate being more preferable. The amount of excipient used is preferably 5 to 60 parts by weight, and more preferably 10 to 30 parts by weight per 100 parts by weight of the composition or formulation.

It should be noted that when the formulation of the present invention has a coating film (e.g., a coated tablet), the amount used is based on the total amount of the components covered with the coating film (or the total amount of the components covered with a coating).

Examples of the binder that can be contained in the granules (i) in the present invention include hydroxypropylcellulose, polyvinylpyrrolidone, macrogol, and similar compounds as listed for the excipient. Specific examples of the binder include hydroxypropylcellulose, hydroxypropylmethylcellulose, methylcellulose, povidone (polyvinylpyrrolidone), and powdered acacia, and preferably hydroxypropylcellulose. The amount of the binder used is preferably 0.1 to 50 parts by weight, more preferably 0.5 to 40 parts by weight, and even more preferably 0.5 to 10 parts by weight, per 100 parts by weight of the composition or formulation.

It should be noted that when the formulation of the present invention has a coating film (e.g., a coated tablet), the amount used is based on the total amount of the components covered with the coating film (or the total amount of the components covered with a coating).

The binder may be contained in granules and external additive components, and is preferably hydroxypropylcellulose.

Suitable examples of the lubricant that can be contained in the granules (i) in the present invention include magnesium stearate, calcium stearate, talc, sucrose fatty acid ester, and sodium stearyl fumarate.

Examples of the stabilizer that can be contained in the granules (i) in the present invention include p-hydroxybenzoate esters such as methylparaben and propylparaben; alcohols such as chlorobutanol, benzyl alcohol, and phenylethyl alcohol; benzalkonium chloride; phenols such as phenol and cresol; thimerosal; dehydroacetic acid; and sorbic acid.

Examples of the flavoring agent that can be contained in the granules of the present invention include sweeteners, acidulants, and flavors commonly used.

A further another aspect of the present invention is a pharmaceutical composition comprising a poorly soluble basic agent, an anionic surfactant, and a basic substance. By adding the basic substance, dissolution of the poorly soluble basic agent is improved and a composition suitable for a high dose formulation can be obtained.

The term "poorly soluble" refers to a solubility of 1 mg/ml or less, more preferably 100 μg/ml or less, even more preferably 10 μg/ml or less, particularly preferably 1 μg/ml or less, and most preferably 0.1 μg/ml or less, in a solvent, particularly water, a buffer, or a gastrointestinal fluid. The basic agent is preferably poorly soluble in any solvent having a pH of 7 or less, more preferably poorly soluble in any solvent having a pH of 4 to 7, and even more preferably poorly soluble in any solvent having a pH of 4 and/or 7. However, when the basic agent is a compound having a basic group in the molecule, it is preferably poorly soluble in any solvent having a pH of 7 or more, more preferably poorly soluble in any solvent having a pH of 7 to 9, and even more preferably poorly soluble in any solvent having a pH of 7 and/or 9. Solvents used to measure a solubility are not limited to particular solvents. Examples of solvents having a pH of 4 include an acetate buffer and a citrate buffer. Examples of solvents having a pH of 5 include an acetate buffer, a citrate buffer, and a phosphate buffer. Examples of solvents having a pH of 7 include water and a phosphate buffer. Examples of solvents having a pH of 9 include a carbonate buffer. The solubility is measured at a temperature of preferably 20 to 40° C., and more preferably 37° C. in any case.

The "basic agent" has at least one basic group, for example, a primary amino group (—NH2), a secondary amino group (imino group, —NH—), a tertiary amino group (>N—), an amide group, and a basic nitrogen-containing heterocyclic group (pyrrolyl, imidazolyl, pyrazolyl, pyrazinyl, purinyl, quinolyl, pyridyl, piperidino, piperidyl, piperazinyl, triazolo group, and the like). It should be noted that the amino group includes a hydrazino group (—NH—NH2), a hydrazo group (—NH—NH—), and the like. The basic agent is required to have at least one basic group and may have the same or different types of more than one basic group. Drugs may form a salt (e.g., salts of inorganic acids such as hydrochloric acid, sulfuric acid, and phosphoric acid; organic carboxylic acids such as acetic acid, tartaric acid, citric acid, fumaric acid, and maleic acid; and organic sulfonic acids such as mesylic acid). Cationic or basic drugs include drugs that generate cationic or basic metabolites or prodrugs which exhibit activity within a living body.

The basic agent is not limited to particular types. The basic agent may be, for example, drugs acting on the central nervous system, the autonomic nervous system, the respiratory system, the circulatory system, the gastrointestinal system, the metabolic system, and other systems, and may be drugs acting on blood and hematopoiesis, ophthalmologic drugs, otolaryngological drugs, or bioactive substances (autacoids). Specific examples of the types of the basic agent include antipyretic agents, analgesic agents, anti-inflammatory agents, sedative-hypnotic agents, antirheumatic agents, antidepressant agents, antiepileptic agents, antidizziness agents, antiallergic agents, cardiotonic agents, β-blockers, calcium antagonists, antiarrhythmic agents, diuretic agents, antianginal agents, therapeutic agents for heart failure, therapeutic agents for myocardial infarction, antihypertensive agents (therapeutic agents for hypertension), therapeutic agents for peripheral circulatory disturbance, vasopressor agents (therapeutic agents for hypotension), bronchodilator agents, antiasthmatic agents, antituberculous agents, antidiabetic agents, therapeutic agents for diabetic complication, antihyperlipidemic agents, antihyperuricemic agents, antitussive and expectorant combinations, antiulcer agents, therapeutic agents for thyroid disease, therapeutic agents for prostatic hyperplasia, anticancer agents, therapeutic agents for osteoporosis, therapeutic agents for Alzheimer's disease, antibiotics, vitamins, and antiplasmin agents.

Specific examples of the basic agent include antipyretic, analgesic, and anti-inflammatory agents (such as antipyretic analgesics including dimetotiazine mesylate; headache relief drugs including dihydroergotamine mesilate, lomerizine hydrochloride, and sumatriptan succinate; and anti-inflammatory agents including fenamic acid, mefenamic acid, floctafenine, proglumetacin maleate, epirizole, and tiaramide hydrochloride), antirheumatic agents (such as penicillamine and methothrexate), antihyperuricemic agents (such as allopurinol), sedative-hypnotic agents (such as rilmazafone hydrochloride and zolpidem tartrate), antidepressant agents (such as nortriptyline hydrochloride, imipramine hydrochloride, amitriptyline hydrochloride, clomipramine hydrochloride, fluvoxamine maleate, and milnacipran hydrochloride), antidizziness agents (such as isoprenaline hydrochloride and betahistine mesilate), antiallergic agents (such as antihistamines including diphenhydramine hydrochloride, diphenylpyraline teoclate, clemastine fumarate, chlorpheniramine maleate, alimemazine tartrate, and promethazine hydrochloride; and histamine H1 antagonists (or basic antiallergic agents) including ketotifen fumarate, azelastine hydrochloride, and epinastine hydrochloride), cardiotonic agents (such as denopamine and isoprenaline hydrochloride), antianginal agents (such as nicorandil, etafenone hydrochloride, dipyridamole, trapidil, and trimetazidine hydrochloride), β-blockers (such as propranolol hydrochloride, difenidol hydrochloride, bufetolol hydrochloride, bupranolol hydrochloride, bopindolol malonate, oxprenolol hydrochloride, alprenolol hydrochloride, indenolol hydrochloride, acebutolol hydrochloride, and celiprolol hydrochloride), calcium antagonists (such as manidipine hydrochloride, benidipine hydrochloride, amlodipine besylate, verapamil hydrochloride, and diltiazem hydrochloride), antiarrhythmic agents (such as aprindine hydrochloride, pilsicainide hydrochloride, propafenone hydrochloride, amiodarone hydrochloride, nifekalant hydrochloride, sotalol hydrochloride, and bepridil hydrochloride), diuretic agents (such as hydrochlorothiazide, penflutizide, benzylhydrochlorothiazide, bumetanide, azosemide, and triamterene), antihypertensive agents (such as sympatholytic agents including clonidine hydrochloride, methyldopa, guanabenz acetate, guanfacine hydrochloride, reserpine, prazosin hydrochloride, bunazosin hydrochloride, terazosin hydrochloride, and doxazosin mesylate; vasodilator agents including hydralazine hydrochloride, budralazine, todralazine hydrochloride, and cadralazine; ACE inhibitors including enalapril maleate, delapril hydrochloride, lisinopril, and benazepril hydrochloride; and angiotensin II receptor antagonists including candesartan cilexetil and valsartan), therapeutic agents for peripheral circulatory disturbance (such as inositol hexanicotinate, hepronicate, tolazoline hydrochloride, and isoxsuprine hydrochloride), vasopressor agents (such as metaraminol bitartrate, methoxamine hydrochloride, midodrine hydrochloride, amezinium metilsulfate, etilefrine hydrochloride, and phenylephrine hydrochloride), bronchodilator agents and antiasthmatic agents (such as β2-adrenergic receptor agonists including ephedrine hydrochloride, methylephedrine hydrochloride, isoprenaline hydrochloride, orciprenaline sulfate, clorprenaline hydrochloride, salbutamol hydrochloride, terbutaline hydrochloride, formoterol fumarate, tulobuterol hydrochloride, fenoterol hydrobromide, procaterol hydrochloride, and clenbuterol hydrochloride; and xanthine derivatives including theophylline, aminophylline, choline theophylline, and proxyphylline), antitussive agents (such as dimemorfan phosphate, tipepidine hibenzate, oxeladin citrate, dextromethorphan hydrobromide, pentoxyverine citrate, cloperastine, and benproperine phosphate), antidiabetic agents (such as tolbutamide, acetohexamide, glibenclamide, glimepiride, buformin hydrochloride, metformin hydrochloride, pioglitazone hydrochloride, and voglibose), expectorants (such as L-methylcysteine hydrochloride, ambroxol hydrochloride, and bromhexine hydrochloride), antiulcer agents (such as H2 receptor antagonists including cimetidine, ranitidine hydrochloride, and famotidine; proton pump inhibitors including lansoprazole and omeprazole; and muscarinic receptor antagonists including pirenzepine hydrochloride), antibiotics (such as clarithromycin, kitasamycin, josamycin, midecamycin, rokitamycin, and azithromycin), narcotics (such as amphetamine and meperidine), vitamins [such as vitamin B1 including thiamine hydrochloride, thiamine nitrate, dicethiamine hydrochloride, cycotiamine, benfotiamine, bisibuthiamine, fursultiamin, prosultiamine, octotiamine, bisbentiamine, and thiamine disulfide; vitamin B2 including riboflavin, riboflavin sodium phosphate, riboflavin butyrate, and flavin-adenine dinucleotide sodium; vitamin B6 including pyridoxine hydrochloride, pyridoxine acetate, and pyridoxal phosphate; nicotinic acids including nicotinic acid and nicotinamide; vitamin B12 including mecobalamin, cyanocobalamin, hydroxocobalamin (such as hydroxocobalamin hydrochloride and hydroxocobalamin acetate), and methylcobalamin; folic acid, pantothenic acid, biotin, vitamin P (such as hesperidin)], and antiplasmin agents (such as epsilon-aminocaproic acid and tranexamic acid).

The basic agents can be used alone or in combinations or two or more depending on the purpose of prevention or treatment.

The present invention also includes:

a composition that consists of a poorly soluble basic agent, an anionic surfactant, and a basic substance and has good dissolution of the agent;

a composition that consists of a poorly soluble basic agent, an anionic surfactant, and a basic substance and has good disintegration of the agent;

the above-mentioned composition that is a formulation for oral administration; and the above-mentioned composition that is a tablet.

The present invention further includes:

a method of improving dissolution of a basic agent by adding a basic substance into a formulation comprising the basic agent and an anionic surfactant;

a method of improving disintegration of a formulation comprising a basic agent and an anionic surfactant by adding a basic substance into the formulation; and a method of producing a formulation that comprises a basic agent and an anionic surfactant and has good dissolution of the agent, comprising adding a basic substance into the formulation.

It has been found that, in the present invention, when a basic drug substance and an anionic surfactant are contained, the basic substance and the anionic surfactant ionically interact to form an impermeable film thereby resulting in poor disintegration and that a basic substance suppresses the formation of the impermeable film.

By adding a basic substance to a formulation comprising a poorly soluble basic agent such as the compound represented by formula (I), and a surfactant, a formulation having good dissolution is obtained. The term "good dissolution" means that a formulation has a dissolution rate of 45% or more, preferably 60% or more, and more preferably 75% or more at 30 minutes when the dissolution test (dissolution test 1) by the paddle method for dissolution test specified in the Japanese Pharmacopeia is performed at 100 revolutions per minute, typically in a test solution, which is purified water (900 mL) containing formic acid (33 mL) and polyoxyethylene (10) octylphenyl ether (2%). Alternatively, the term "good dissolution" means that a formulation has a dissolution rate of 45% or more, preferably 60% or more, and more preferably 75% or more at 30 minutes when the dissolution test (dissolution test 2) by the paddle method is performed at 100 revolutions per minute in a test solution, which is 900 mL of the 1st fluid for dissolution test specified in the Japanese Pharmacopeia containing polyoxyethylene (10) octylphenyl ether (4%), or preferably 75 mL of the 1st fluid for dissolution test containing about 3 g of polyoxyethylene (10) octylphenylether. Preferably, the term "good dissolution" means that a formulation has the above-mentioned dissolution in either dissolution test 1 or dissolution test 2 and more preferably means that a formulation has a dissolution rate of 45% or more, preferably 60% or more, and more preferably 75% or more at 30 minute when dissolution test 2 is performed. Particularly preferably, the term "good dissolution" means that 70% or more of a formulation is dissolved at 75 minutes when dissolution test 2 is performed.

It should be noted that the 1st fluid for dissolution test specified in the Japanese Pharmacopeia is a colorless clear solution that contains sodium chloride (2.0 g) in hydrochloric acid (7.0 ml) and water (q.s. to 1000 mL) and has a pH of about 1.2.

The term "improving dissolution" means that a dissolution of the agent below the dissolution range described above is increased to the dissolution range. Improving dissolution facilitates efficient absorption of the pharmaceutically active ingredient to rapidly exert drug efficacy. In countries, except Japan, including the United States, Europe, and Israel, the dissolution test 2 is prescribed to be a standard testing methodology for dissolution of an approved capsule formulation containing a pharmaceutically active ingredient. A desirable dissolution rate in the dissolution test 2 is 45% or more at 30 minutes and 75% or more at 70 minutes in the dissolution test in the United States and Israel, and is 45% or more and 75% or less at 30 minutes, and 75% or more at 70 minutes in the dissolution test in the EU region.

According to the present invention, when a basic substance is added to a formulation comprising a poorly soluble basic agent, such as the compound represented by formula (I), and a surfactant, the resulting formulation has good disintegration. The term "good disintegration" means that a formulation disintegrates within 30 minutes and preferably within 15 minutes in the disintegration test specified in the Japanese Pharmacopeia using, as a test medium, the 1st fluid for dissolution test specified in the Japanese Pharmacopeia (disintegration test 1). Alternatively, the "good disintegration" means that a formulation disintegrates at 10 minutes and preferably within 5 minutes in the disintegration test specified in the Japanese Pharmacopeia using water as a test medium (disintegration test 2). Preferably, the term "good disintegration" means that a formulation has the above-mentioned disintegration in either the disintegration test 1 or disintegration test 2 and more preferably means that a formulation disintegrates within 3 minutes in the disintegration test 2. The term "improving disintegration" means that a disintegration below the disintegration range described above of the formulation is increased to the disintegration range. The term "disintegrate" means that "a residue of a sample is observed and the residue is a minor amount of a soft substance or muddy substance at 30 minutes in a disintegration test" or that "no residue of a sample is observed at 30 minutes in a disintegration test", and preferably means that no residue of a sample is observe at 30 minutes in a disintegration test.

EXAMPLES

The present invention will be now described in more detail in Examples below; however, the present invention is not limited by the Examples. It should be noted that sodium lauryl sulfate used in Examples 1-20 was NIKKOL SLS (Nikko Chemicals Co., Ltd.).

Reference Example 1: Formation of Impermeable Film (Production of Formulation)

In accordance with the amounts of components shown in Table 1, tablets were prepared. Hydrochloride of the compound of formula (I) (hereinafter referred to as Compound A), sodium lauryl sulfate, and magnesium stearate were manually mixed together in a polyethylene vessel. The powder mixture was compressed under a pressure of 500 kgf in a static pressure-type tablet press machine (P-16, RIKEN SEIKI) to form tablets (ϕ=9.0 mm) each containing 150 mg of Compound A in terms of the free form.

TABLE 1

| Amount blended per tablet, mg | |
|---|---|
| Components | Reference Example 1 |
| Compound A | 161.330 |
| Sodium lauryl sulfate | 37.500 |
| Magnesium stearate*[1] | 1.170 |
| Total | 200.00 |

*[1]Trade name: Parteck LUB MST, purchased from Merck (Evaluation of Formulation and Results)

The formulation of Reference Example 1 was subjected to the dissolution test (dissolution test 2) via the paddle method for dissolution test specified in the Japanese Pharmacopeia performed at 100 rotations/minute using, as a test medium, 900 mL of the 1st fluid for dissolution test specified in the Japanese Pharmacopeia containing polyoxyethylene (10)

octyl phenyl ether (4%). The dissolution profile of Reference Example 1 is shown in FIG. 1. Photographs of appearance of the formulation before and after the test and a photograph of a midsection after the test are shown in FIG. 2.

As shown in FIG. 1, the tablets that were formed by wet granulation and contained Compound A and sodium lauryl sulfate had a linear dissolution profile and the maximum dissolution rate of 40% or less. As shown in FIG. 2, the formulation after the test was cut in the middle of the tablet, resulting in the observation that the test medium permeated only the surface of the tablet and the interior of the tablet remained dry. This is probably resulted from an impermeable film that was formed on the surface of the tablet. The impermeable film probably prevented the test medium from permeating the interior of the tablet and failed to continue disintegration and to result in a good dissolution profile. It should be noted that the impermeable film refers to a film that is formed on the surface of the tablet by a basic agent and an anionic surfactant in a test medium.

Examples 1 to 7: Investigation of Disintegration of Basic Substances (Production of Formulation)

In accordance with the amounts of components for tablet formulation shown in Table 2, tablets were prepared. X included in the external additive components in the formulation was a substance shown in Table 3. Components formulated for granules were mixed together, and the premixed powder was placed in a stainless beaker. Purified water was added while stirring with a metallic spatula to perform wet granulation and dry it in a vacuum dryer (VOS-301SD, TOKYO RIKAKIKAI CO, LTD) at ordinary temperature. Subsequently, this was sized with a sieve having a size diameter of 850 μm to obtain granules that were further mixed with external additive components to obtain a powder mixture. The powder mixture was compressed under a pressure of 1000 kgf in a static pressure-type tablet press machine (P-16, RIKEN SEIKI) to form tablets (15.9×8.4 mm) each containing 300 mg of Compound A in terms of the free form. It should be noted that Comparative Example 1 was a tablet that was formed according to the capsule formulation described in Patent Literature 5. The relationship between the type of X and the disintegration time of tablet was investigated by comparing Comparative Example 1 with Examples 1 to 7.

TABLE 2

| Amount blended per tablet, mg | |
|---|---|
| Formulation of tablet | Examples 1-7 |
| Components formulated for granules | |
| Compound A | 322.7 |
| Carmellose calcium*[1] | 30.0 |
| Hydroxypropylcellulose*[2] | 30.0 |
| Sodium lauryl sulfate*[3] | 75.0 |
| [Purified water]*[4] | — |
| External additive components | |
| X*[5] | 142.3 |
| Carmellose calcium | 56.7 |
| Magnesium stearate | 3.3 |
| Total | 660.0 |

*[1]Trade name: E.C.G-505 (GOTOKU CHEMICAL COMPANY LTD.)

*[2]Trade name: NISSO HPC (Nippon Soda Co., Ltd.)

*[3]Trade name: NIKKOL SLS (Nikko Chemicals Co., Ltd.)

*[4]Purified water was removed via drying

*[5]Additives described in Table 3

TABLE 3

| Comparative Example/ Example | Compound Name | Trade Name | Purchased from |
|---|---|---|---|
| | A list of substances used for X | | |
| Comparative Example 1 | Lactose hydrate | Pharmatose 200M | DFE Pharma |
| Example 1 | L-arginine | L-arginine | AJINOMOTO HEALTHY SUPPLY CO., INC. |
| Example 2 | Meglumine | Meglumine Emprove ® api | Merck |
| Example 3 | Magnesium aluminometasilicate | Neusilin* | Fuji Chemical Industries Co., Ltd. |
| Example 4 | Magnesium oxide | Magnesium oxide | Kyowa Chemical Industry Co., Ltd. |
| Example 5 | Magnesium hydroxide | Magnesium hydroxide | Kyowa Chemical Industry Co., Ltd. |
| Example 6 | Magnesium carbonate | Magnesium carbonate | Kyowa Chemical Industry Co., Ltd. |
| Example 7 | Sodium bicarbonate | Sodium bicarbonate | Kyowa Chemical Industry Co., Ltd. |

*Neusilin(R) US2 and S2 (Fuji Chemical Industries Co., Ltd.) were each used as magnesium aluminometasilicate.

The formulations of Comparative Example 1 and Examples 1 to 7 were each subjected in triplicate to the disintegration test specified in the Japanese Pharmacopeia performed using, as a test medium, water or 1st fluid for dissolution test specified in the Japanese Pharmacopeia. Disintegration behaviors of Examples 1 to 7 are shown in Table 4. It should be noted that this disintegration test was performed in water (disintegration test 2) or under acidic condition (disintegration test 1) in which disintegration proceeded more slowly than in water. In the specification, symbols used in the following table are defined as follows:

–: a residue of the sample is observed at 30 minutes in the disintegration test.

+: a residue of the sample is observed and the residue is a minor amount of a soft substance or a muddy substance at 30 minutes in the disintegration test.

++: no residue of the sample is observed as 30 minutes in the disintegration test.

TABLE 4

| Disintegratability for Comparative Example 1 and Examples 1-7 | | | |
|---|---|---|---|
| | | Results | |
| Comparative Example/ Example | Compound Name | Water | 1st fluid for dissolution test specified in the Japanese Pharmacopeia |
| Comparative Example 1 | Lactose hydrate | − | − |
| Example 1 | L-arginine | ++ | + |
| Example 2 | Meglumine | ++ | + |
| Example 3 | Magnesium aluminometasilicate | ++ | ++ |
| Example 4 | Magnesium oxide | ++ | ++ |
| Example 5 | Magnesium hydroxide | ++ | + |
| Example 6 | Magnesium carbonate | ++ | ++ |
| Example 7 | Sodium bicarbonate | ++ | + |

(Evaluation of Formulation and Results)

As shown in Table 4, in Examples 1 to 7, tablets formed using a basic substance as X had better disintegration than the tablet of Comparative Example 1.

Examples 8 to 10: Investigation of the Production Processes on Dissolution (Production of Formulation)

In accordance with the amounts of components for tablet formulation shown in Table 5, tablets were prepared with different production processes. In Example 8, formulated components were mixed together to obtain a powder mixture. In Example 9, components formulated for granules were mixed together and compressed under a pressure of 400 kgf in a static pressure-type tablet press machine (P-16, RIKEN SEIKI) with a mallet having ϕ16 mm. The resulting molded products were sized with a sieve having a size diameter of 850 μm to obtain granules that were further mixed with external additive components to provide a powder mixture. In Example 10, formulated components shown in Table 5 were mixed together, and the pre-mixed powder was placed in a stainless beaker. Purified water was added while stirring with a metallic spatula to perform wet granulation and dry it in a vacuum dryer (VOS-301SD, TOKYO RIKAKIKAI CO, LTD) at ordinary temperature. Subsequently, this was sized with a sieve having a mesh size of 850 μm to obtain granules that were further mixed with external additive components to obtain a powder mixture. Each of the powder mixtures of Examples 8 to 10 was compressed under a pressure of 500 kgf in a static pressure-type tablet press machine (P-16, RIKEN SEIKI) to form tablets each containing 150 mg of Compound A in terms of the free form. Tablets formed with production processes in which a basic substance was additionally used for formulated components were investigated for the dissolution.

(Evaluation of Formulation and Results)

As shown in FIG. 3, in Examples 8 to 10, regardless of production processes, that is whether granules were formed or not, tablets formed using a basic substance as a formulated component had better dissolution than the tablet of Comparative Example 1. These results meet the standards of dissolution tests in various countries for an approved capsule formulation.

TABLE 5

| | Amount blended per tablet, mg | | | |
|---|---|---|---|---|
| Components blended | Example 8 | | Example 9 | Example 10 |
| | | Components blended for granules | | |
| Compound A | 161.35 | Compound A | 161.35 | 161.35 |
| Carmellose calcium | 43.35 | Carmellose calcium | 15.00 | 15.00 |
| Hydroxypropylcellulose | 15.00 | Hydroxypropylcellulose | 15.00 | 15.00 |
| Sodium lauryl sulfate | 37.50 | Sodium lauryl sulfate | 37.50 | 37.50 |
| | | [Purified water]*[1] | — | q.s. |
| | | External additive components | | |
| Magnesium aluminometasilicate | 71.15 | Magnesium aluminometasilicate | 71.15 | 71.15 |
| Carmellose calcium | — | Carmellose calcium | 28.35 | 28.35 |
| Magnesium stearate | 1.65 | Magnesium stearate | 1.65 | 1.65 |
| Total | 330 | Total | 330 | 330 |

*[1]Purified water was removed via drying.

Examples 11 to 14: Investigation of the Proportions of Excipients and Basic Substances on Dissolution (Production of Formulation)

In accordance with the amounts of components shown in Table 6, components formulated for granules were mixed together, and purified water was added to the pre-mixed powder to perform wet granulation in a similar manner to Examples 1 to 7. The granulated powders obtained from wet granulation were dried and sized with a sieve having a size diameter of 850 μm to obtain granules that were further mixed with external additive components to obtain a powder mixture. The powder mixture was compressed under a pressure of 1000 kgf in a static pressure-type tablet press machine (P-16, RIKEN SEIKI) to form tablets (15.9×8.3 mm) each containing 300 mg of Compound A in terms of the free form. These tablets were investigated for the proportions of excipients to components formulated for granules and proportions of disintegrators to a basic substance contained in external additive components on the dissolution.

TABLE 6

| | Amount blended per tablet, mg | | | |
|---|---|---|---|---|
| | Example 11 | Example 12 | Example 13 | Example 14 |
| Components blended for granules | | | | |
| Compound A | 322.7 | 322.7 | 322.7 | 322.7 |
| Carmellose calcium | 30.0 | 30.0 | 30.0 | 30.0 |
| Hydroxypropylcellulose | 30.0 | 30.0 | 30.0 | 30.0 |
| Sodium lauryl sulfate | 75.0 | 75.0 | 75.0 | 75.0 |
| Lactose monohydrate | 72.3 | — | 22.3 | — |
| Crystalline cellulose | — | 72.3 | — | — |
| [Purified water]*1 | q.s. | q.s. | q.s | q.s. |
| External additive components | | | | |
| Magnesium stearate | 3.3 | 3.3 | 3.3 | 3.3 |
| Crospovidone*2 | 56.7 | 56.7 | 56.7 | 129.0 |
| Magnesium aluminometasilicate | 70.0 | 70.0 | 120.0 | 70.0 |
| Total | 660 | 660 | 660 | 660 |

*1Purified water was removed via drying.
*2Trade name: Polyplasdone XL (Ashland)

(Evaluation of Formulation and Results)

In Examples 11 to 14, the dissolution test (dissolution test 1) via the paddle method for dissolution test specified in the Japanese Pharmacopeia was performed at 100 revolutions per minute, in a test solution, which is purified water (900 mL) containing formic acid (33 mL) and polyoxyethylene (10) octylphenyl ether (2%). The dissolution profiles of Examples 11 to 14 are shown in FIG. 4.

As shown in FIG. 4, addition of a basic substance (magnesium aluminometasilicate) resulted in a good dissolution profile regardless of types of excipients included in components formulated for granules and proportions of the disintegrators.

Examples 15 to 18: Investigation of the Combination of Excipients and External Additive Components on Dissolution (Production of Formulation)

In accordance with the amounts of components shown in Table 7, components formulated for granules were weighed and mixed together in a granulator (VG-05, Powrex Corporation), purified water was added to perform granulation and dry it in a fluidized bed dryer (FL-LABO, inlet air temperature, 60° C.) to achieve a loss on drying of 2% or less. The resulting dried powder was sized in a screen mill with a screen having a mesh size diameter of 1.4 mm to obtain granules and the granules were further mixed with external additive components to obtain a powder mixture. The powder mixture was compressed in a static pressure-type tablet press machine under a similar condition to those of Examples 8 to 10 to form tablets each containing 150 mg of Compound A in terms of the free form. The tablets were investigated for dissolution.

TABLE 7

| | Amount blended per tablet, mg | | | |
|---|---|---|---|---|
| Components blended | Example 15 | Example 16 | Example 17 | Example 18 |
| Components blended for granules | | | | |
| Compound A | 161.3 | 161.3 | 161.3 | 161.3 |
| Hydroxypropylcellulose | 15.0 | 15.0 | 15.0 | 15.0 |
| Sodium lauryl sulfate | 37.5 | 37.5 | 37.5 | 37.5 |
| Carmellose calcium | 15.0 | — | 15.0 | — |
| Crospovidone | — | 15.0 | — | 15.0 |
| Lactose hydrate | 36.2 | 36.2 | — | — |
| D-mannitol*1 | — | — | 36.2 | 36.2 |
| [Purified water] *2 | q.s. | q.s. | q.s. | q.s. |
| External additive components | | | | |
| Magnesium stearate | 1.7 | 1.7 | 1.7 | 1.7 |
| Carmellose calcium | 28.4 | — | 28.4 | — |

TABLE 7-continued

| Amount blended per tablet, mg | | | | |
|---|---|---|---|---|
| Components blended | Example 15 | Example 16 | Example 17 | Example 18 |
| Crospovidone | — | 28.4 | — | 28.4 |
| Magnesium aluminometasilicate | 35.0 | 35.0 | 35.0 | 35.0 |
| Total | 330 | 330 | 330 | 330 |

*[1]Trade name: Parteck M200(Merck)
*[2] Purified water was removed via drying.

(Evaluation of Formulation and Results)

In Examples 15 to 18, the disintegration test (disintegration test 1) specified in the Japanese Pharmacopeia was performed using, as a test medium, 1st fluid for dissolution test specified in the Japanese Pharmacopeia. For all of the tablets of Examples 15 to 18, no residue of the sample was observed at 30 minutes in the disintegration test. It should be noted that this disintegration test (disintegration test 1) was performed under acidic condition in which disintegration proceeded more slowly than in water.

In Examples 15 to 18, the dissolution test (dissolution test 2) was performed by the paddle method for dissolution test specified in the Japanese Pharmacopeia at 100 revolutions per minute using, as a test medium, 900 mL of 1st fluid for dissolution test specified in the Japanese Pharmacopeia containing polyoxyethylene (10) octylphenyl ether (4%). The dissolution profiles of Examples 15 to 18 are shown in FIG. 5.

As shown in FIG. 5 showing the dissolution profiles of Compound A from tablets, addition of magnesium aluminometasilicate resulted in good dissolution regardless of the combination of the excipients and the disintegrators. These results meet standards of dissolution tests in various countries for approved capsule formulations.

Examples 19 and 20: Investigation of the Weight of Tablet (Production of Formulation)

In accordance with the amounts of components shown in Table 8, components formulated for granules were each weighed and mixed together in a fluidized bed dryer granulator (FG-602, Freund Corporation). Purified water was added via spraying to perform granulation and dry it in the dryer granulator at a temperature of supplied air of 60° C. to achieve a loss on drying of 2% or less. The resulting dried powder was sized in a particle-size selector with a screen having a size diameter of 1.4 mm to obtain granules and the obtained granules were further mixed with external additive components to obtain a powder mixture. The powder mixture was compressed under a pressure of 10 kN in a rotary tablet press machine (AQUARIUS-C, KIKUSUI SEISAKUSHO LTD.) to form tablets (17.3×8.0 mm) each containing 300 mg of Compound A in terms of the free form. The relationship between the tablet weight and disintegration was investigated by comparing these tablets with those of Examples 15 to 18.

TABLE 8

| Amount blended per tablet, mg | | |
|---|---|---|
| Components blended | Example 19 | Example 20 |
| Components blended for granules | | |
| Compound A | 322.7 | 322.7 |
| Hydroxypropylcellulose | 29.7 | 29.7 |

TABLE 8-continued

| Amount blended per tablet, mg | | |
|---|---|---|
| Components blended | Example 19 | Example 20 |
| Sodium lauryl sulfate | 75.0 | 75.0 |
| Carmellose calcium | — | 29.7 |
| Crospovidone | 29.7 | — |
| Lactose hydrate | 72.6 | — |
| D-mannitol | — | 72.6 |
| [Purified water] *[1] | q.s. | q.s. |
| External additive components | | |
| Magnesium stearate | 3.3 | 3.3 |
| Carmellose calcium | — | 57.0 |
| Crospovidone | 57.0 | — |
| Magnesium aluminometasilicate | 70.0 | 70.0 |
| Total | 660 | 660 |

*[1] Purified water was removed via drying.

The tablets of Examples 19 and 20 were each subjected to the disintegration test specified in the Japanese Pharmacopeia performed using, as a test medium, 1st fluid for dissolution test specified in the Japanese Pharmacopeia. In the tablets of Examples 19 and 20, no residue of the sample was observed at 30 minutes in the disintegration test. It should be noted that this disintegration test (disintegration test 1) was performed under acidic condition in which disintegration proceeded more slowly than in water.

(Evaluation of Formulation and Results)

Addition of a basic substance, magnesium aluminometasilicate resulted in good disintegration similar to that in Examples 15 to 18 although the tablet weight was increased.

The invention claimed is:

1. A tablet comprising a pharmaceutical composition comprising a compound represented by formula (I) or a salt thereof, a surfactant, a disintegrator, and a basic substance

[Formula 1]

(I)

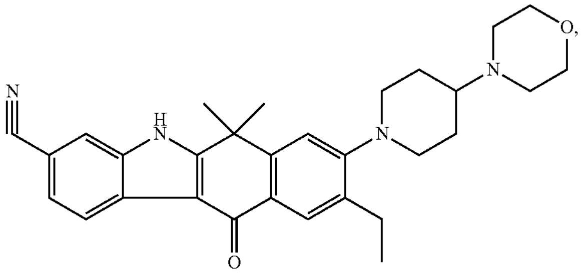

wherein the basic substance is at least one substance selected from the group consisting of magnesium aluminometasilicate, L-arginine, meglumine, magnesium oxide, magnesium hydroxide, and magnesium carbonate, wherein the surfactant is sodium lauryl sulfate, and wherein the tablet contains the compound represented by formula (I) or a salt thereof in an amount of 150 mg to 800 mg per unit formulation in terms of the free form and contains the disintegrator in an amount of 5 wt % or more based on the total amount of the pharmaceutical composition.

2. The tablet according to claim 1, wherein the disintegrator is at least one substance selected from the group consisting of carmellose calcium, crospovidone, sodium starch glycolate, and croscarmellose sodium.

3. The tablet according to claim 1, wherein the pharmaceutical composition comprises a weight ratio of the compound represented by formula (I) or a salt thereof to the surfactant at a range from 100:3 to 100:50.

4. The tablet according to claim 1, wherein the pharmaceutical composition contains the basic substance in an amount of 5 wt % or more.

5. The tablet according to claim 1, wherein a dissolution rate at 30 minutes is 45% or more as measured by the paddle method for dissolution test specified in the Japanese Pharmacopeia, using the 1st fluid for dissolution test specified in the Japanese Pharmacopeia containing polyoxyethylene (10) octylphenyl ether (4%).

6. The tablet according to claim 1, wherein a dissolution rate at 30 minutes is 60% or more as measured by the paddle method for dissolution test specified in the Japanese Pharmacopeia, using the 1st fluid for dissolution test specified in the Japanese Pharmacopeia containing polyoxyethylene (10) octylphenyl ether (4%).

7. The tablet according to claim 1, wherein a dissolution rate at 30 minutes is 75% or more as measured by the paddle method for dissolution test specified in the Japanese Pharmacopeia, using the 1st fluid for dissolution test specified in the Japanese Pharmacopeia containing polyoxyethylene (10) octylphenyl ether (4%).

8. The tablet according to claim 1, wherein a dissolution rate at 75 minutes is 70% or more as measured by the paddle method for dissolution test specified in the Japanese Pharmacopeia, using the 1st fluid for dissolution test specified in the Japanese Pharmacopeia containing polyoxyethylene (10) octylphenyl ether (4%).

9. The tablet according to claim 1, wherein a dissolution rate at 30 minutes is 45% or more as measured by the paddle method for dissolution test specified in the Japanese Pharmacopeia, using purified water (900 mL) containing formic acid (33 mL) and polyoxyethylene (10) octylphenyl ether (2%).

10. The tablet according to claim 1, wherein a dissolution rate at 30 minutes is 60% or more as measured by the paddle method for dissolution test specified in the Japanese Pharmacopeia, using purified water (900 mL) containing formic acid (33 mL) and polyoxyethylene (10) octylphenyl ether (2%).

11. The tablet according to claim 1, wherein a dissolution rate at 30 minutes is 75% or more as measured by the paddle method for dissolution test specified in the Japanese Pharmacopeia, using purified water (900 mL) containing formic acid (33 mL) and polyoxyethylene (10) octylphenyl ether (2%).

12. The tablet according to claim 1, wherein a dissolution rate at 75 minutes is 70% or more as measured in the paddle method for dissolution test specified in the Japanese Pharmacopeia, using purified water (900 mL) containing formic acid (33 mL) and polyoxyethylene (10) octylphenyl ether (2%).

13. The tablet according to claim 1, wherein a residue of a sample is observed at 30minutes in the disintegration test specified in the Japanese Pharmacopeia using water as a test medium, wherein the residue is a minor amount of a soft substance or a muddy substance.

14. The tablet according to claim 1, wherein no residue of a sample is observed at 30minutes in the disintegration test specified in the Japanese Pharmacopeia using water as a test medium.

15. The tablet according to claim 1, wherein a residue of a sample is observed at 30minutes in the disintegration test specified in the Japanese Pharmacopeia using, as a test medium, the 1st fluid for dissolution test specified in the Japanese Pharmacopeia, wherein the residue is a minor amount of a soft substance or a muddy substance.

16. The tablet according to claim 1, wherein no residue of a sample is observed at 30minutes in the disintegration test specified in the Japanese Pharmacopeia using, as a test medium, the 1st fluid for dissolution test specified in the Japanese Pharmacopeia.

* * * * *